United States Patent
Petropoulos

(10) Patent No.: US 11,459,624 B2
(45) Date of Patent: *Oct. 4, 2022

(54) COMPOSITIONS AND METHODS FOR DETERMINING RESISTANCE TO INHIBITORS OF VIRUS ENTRY USING RECOMBINANT VIRUS ASSAYS

(71) Applicant: MONOGRAM BIOSCIENCES, INC., South San Francisco, CA (US)

(72) Inventor: Christos J. Petropoulos, Half Moon Bay, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/780,426

(22) Filed: Feb. 3, 2020

(65) Prior Publication Data

US 2020/0332373 A1     Oct. 22, 2020

Related U.S. Application Data

(63) Continuation of application No. 14/100,467, filed on Dec. 9, 2013, now Pat. No. 10,550,441, which is a continuation of application No. 11/146,879, filed on Jun. 6, 2005, now Pat. No. 8,603,736.

(60) Provisional application No. 60/577,851, filed on Jun. 7, 2004.

(51) Int. Cl.
| | |
|---|---|
| *C12Q 1/70* | (2006.01) |
| *C12N 7/00* | (2006.01) |
| *C07K 14/005* | (2006.01) |
| *G01N 33/50* | (2006.01) |
| *C12Q 1/66* | (2006.01) |
| *C12Q 1/04* | (2006.01) |

(52) U.S. Cl.
CPC ............ *C12Q 1/703* (2013.01); *C07K 14/005* (2013.01); *C12N 7/00* (2013.01); *C12Q 1/70* (2013.01); *G01N 33/5008* (2013.01); *C12N 2740/16021* (2013.01); *C12N 2740/16062* (2013.01); *C12N 2740/16122* (2013.01); *C12N 2770/20021* (2013.01); *C12N 2800/107* (2013.01); *C12N 2800/40* (2013.01); *C12Q 1/04* (2013.01); *C12Q 1/66* (2013.01); *G01N 2333/16* (2013.01); *G01N 2333/162* (2013.01)

(58) Field of Classification Search
CPC ...................................................... C12Q 1/703
See application file for complete search history.

(56) References Cited

U.S. PATENT DOCUMENTS

| | | | |
|---|---|---|---|
| 5,837,464 A | 11/1998 | Capon et al. | |
| 5,922,325 A | 7/1999 | Tilley et al. | |
| 5,939,320 A | 8/1999 | Littman et al. | |
| 6,103,462 A | 8/2000 | Paulous et al. | |
| 6,242,187 B1 | 6/2001 | Capon et al. | |
| 6,406,911 B1 | 6/2002 | Dong | |
| 7,097,970 B2 | 8/2006 | Petropoulos et al. | |
| 7,169,551 B2 | 1/2007 | Petropoulos et al. | |
| 7,235,356 B2 | 6/2007 | Petropoulos et al. | |
| 7,247,439 B1 | 7/2007 | Richman et al. | |
| 7,595,049 B2 | 9/2009 | Steigler et al. | |
| 8,603,736 B2 * | 12/2013 | Petropoulos ............. | C12Q 1/04 435/5 |
| 10,550,441 B2 * | 2/2020 | Petropoulos ........... | C12Q 1/703 |
| 2002/0037500 A1 | 3/2002 | Whitcomb et al. | |
| 2002/0182592 A1 | 12/2002 | Petropoulos et al. | |
| 2004/0110125 A1 | 6/2004 | Petropoulos et al. | |
| 2006/0160185 A1 | 7/2006 | Petropoulos et al. | |
| 2006/0183110 A1 | 8/2006 | Petropoulos et al. | |
| 2014/0272930 A1 | 9/2014 | Petropoulos | |

FOREIGN PATENT DOCUMENTS

| | | |
|---|---|---|
| EP | 2385145 | 11/2011 |
| EP | 2385145 | 10/2018 |
| ES | 2385960 | 8/2012 |
| WO | 97/27319 | 7/1997 |
| WO | 01/81608 | 11/2001 |
| WO | 03/070985 | 8/2003 |

OTHER PUBLICATIONS

Petropoulos, C. J., et al., Apr. 2000, A novel phenotypic drug susceptiblity assay for human immunodeficiency virus type 1, Antimicrob. Agents Chemother. 44(4):920-928.*
Labrosse, B., et al., Jan. 2003, Baseline susceptibility of primary human immunodeficiency virus to entry inhibitors, J. Virol. 77(2):1610-1613.*
U.S. Appl. No. 14/100,467, Final Office Action, dated May 17, 2019, 10 pages.
U.S. Appl. No. 14/100,467, Final Office Action, dated Oct. 19, 2017, 24 pages.

(Continued)

*Primary Examiner* — Jeffrey S Parkin

(74) *Attorney, Agent, or Firm* — Kilpatrick Townsend & Stockton LLP

(57) ABSTRACT

The invention provides a method for determining whether a human immunodeficiency virus is resistant to a viral entry inhibitor. The methods are particularly useful for determining resistance to inhibitors that act by a non-competitive mechanism. In certain aspects, the methods comprise determining whether an HIV population is resistant to an HIV entry inhibitor, comprising determining a log-sigmoid inhibition curve comprising data points for entry of the HIV population in the presence of varying concentrations of the HIV entry inhibitor, wherein if the entry of the HIV population cannot be completely inhibited by the HIV entry inhibitor, the HIV population is resistant to the HIV entry inhibitor.

15 Claims, 12 Drawing Sheets

Figure 1A:
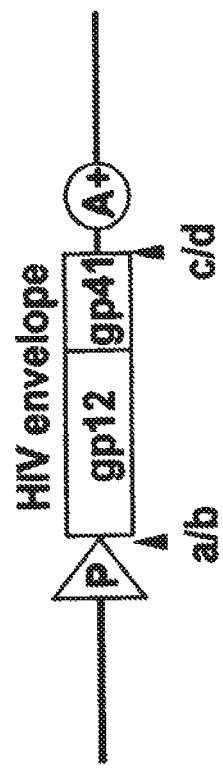

Specification includes a Sequence Listing.

(56) References Cited

OTHER PUBLICATIONS

U.S. Appl. No. 14/100,467, Non-Final Office Action, dated Jan. 8, 2016, 17 pages.
U.S. Appl. No. 14/100,467, Non-Final Office Action, dated Oct. 5, 2018, 25 pages.
U.S. Appl. No. 14/100,467, Non-Final Office Action, dated Jan. 3, 2017, 27 pages.
U.S. Appl. No. 14/100,467, Notice of Allowance, dated Sep. 16, 2019, 5 pages.
EP 18199100.1, Office Action, dated Apr. 21, 2020, 4 pages.
EP 18199100.1, Office Action, dated Apr. 7, 2021, 4 pages.
Adachi et al., 1986, "Production of Acquired Immunodeficiency Syndrome-associated Retrovirus in Human and Nonhuman Cells Transfected with an Infectious Molecular Clone" Journal of Virology, 59:284-291.
Alkhatib et al., 1996, "CC CKR5: ARantes, MIP-1alpha, MIP-1 Beta Receptor as a Fusion Cofactor for Macrophage-tropic Hiv-1" Science, 272:1955-58.
Allaway et al., 1993, "Synergistic Inhibition of HIV-1 Envelope-Mediated Cell Fusion by CD4-based Molecules in Combination with Antibodies to Gp120 or Gp41" Aids Res. Hum. Retroviruses 9:581-87.
Altschul S. et al., 1997, "Gapped BLAST and PSI-BLAST: a new generation of protein database search programs," Nucleic Acids Res., 25:3389-3402.
Altschul, S. et al., 1990, "Basic Local Alignment Search Tool," J. Mol. Biol., 215:403-410.
Auewarakul et al., 2001, "Application of HIV-1 -Green Fluorescent Protein (GFP) Reporter Viruses in Neutralizing Antibody Assays," Asian Pacific Journal of Allergy and Immunology, 19:139-144.
Angarano et al., 2000, "Genotype and phenotype resistance: an overview," J. Biol. Reg. Homeostatic Ag. Wichtig Editore. Milan. IT, 14(1):11-14.
Baba et al., 1999, "A Small-molecule, Nonpeptide CCRS Antagonist with Highly Potent and Selective Anti-hiv-1 Activity," Proc. Natl. Acad. Sci. USA, 96:5698-03.
Barnes, 1994, "PCR amplification of up to 35-kb DNA with high fidelity and high yield from lambda bacteriophage templates," Proc. Natl. Acad. Sci., USA, 91:2216-20.
Baxter et al., 1999, "A Pilot Study of the Short-term Effects of Antiretroviral Management Based on Plasma Genotypic Antiretroviral Resistance Testing (Gart) in Patients Failing Antiretroviral Therapy," Presented at the 6th Conference on Retroviruses and Opportunistic Infections Chicago II.
Bernard and Couturier, 1992, "Cell Killing by the F Plasmid Ccdb protein Involves Poisoning of DNAtopoisomerase II Complexes" J. Mol. Bio. 226:735-45.
Bernard et al., 1993, "The F Plasmid CcdB protein Induces Efficient ATP-dependent DNA Cleavage by Gyrase," J Mol. Biol., 23:534-41.
Billick, E. et al., The Differential Sensitivity of Human and Rhesus Macaque CCR5 to Small-Molecule Inhibitors of Human Immunodeficiency Virus Type 1 Entry Is Explained by a Single Amino Difference and Suggests a Mechanism of Action for These Inhibitors, 2004, J. Virology 78(8):4134-4144.
Bleul et al., 1996, "The Lymphocyte Chemoattractant Sdf-1Is a Ligand for Lestr/fusin and Blocks Hiv-1 Entry," Nature, 382:829-33.
Bridger et al., 1999, "Synthesis and Structure-activity Relationships of Phenylenebis(methylene)-linked Bis-azamacrocycles That Inhibit HIV-1 and HIV-2 Replication by Antagonism of the Chemokine Receptor CXCR4," J. Med. Chem. 42:3971-81.
Carpenter et al., 2000 "Antiretroviral therapy in adults: updated recommendations of the International AIDS Society—USA Panel". JAMA, 283: 381-89.
Centers for Disease Control and Prevention HIV/AIDS Surveillance Report, 1999; 11(No. 1).
Chehimi et al., 1993, "CD4-independent infection of human peripheral blood dendritic cells with isolates of human immunodeficiency virus type 1", Journal of General Virology, 74: 1277-1285.
Cho et al., 2001, "Polyvalent Envelope Glycoprotein Vaccine Elicits a Broader Neutralizing Antibody Response but is Unable to Provide Sterilizing Protection Against Heterologous Simian/Human Immunodeficiency Virus Infection in Pigtailed Macaques" Journal of Virology, 75(5): 2224-2234.
Cilliers et al., 2004; "Sensitivity of HIV type 1 Subtype C Isolates to the Eutiy Inhibitor T-20," Aids Res. Human Retrov. 20(5):477-82.
Coffin, 1995, "HIV Population Dynamics in Vivo: Implications for Genetic Variation, Pathogenesis, and Therapy," Science 267:483-489.
Current Protocols in Molecular Biology, Ausubel, F.M. et al. eds., John Wiley and Sons, Inc., USA, 2010 Table of Contents and list of yearly supplements.
Department of Health and Human Services, 2000, Henry Kaiser Family Foundation: "Guidelines for the Use of Antiretrovirals Agents in HIV-infected Adults and Adolescents".
Dorn et al. 2001, "Antagonists of the Human CCR5 Receptor as Anti-HIV-1 Agents. Part 1: Discovery and Initial Structure-Activity Relationships for 1-Amino-2-phenyl-4-(piperidin-1-yl) butanes," Bioorganic & Medicinal Chemistry Letters 11:259-64.
Dorsky et al., 1996, "Detection of HIV-1 Infection with a Green Fluorescent Protein Reporter System," Journal of Acquired Immune Deficiency Syndromes and Human Retrovirology, 13:308-313.
Eisenberg et al. 1984, "Analysis of Membrane and Surface Protein Sequences with the Hydrophobic Moment Plot," J. Mol. Bioi., 179:125-142.
Finke et al., 2001, "Antagonists of the Human CCR5 Receptor as Anti-HIV-1 Agents. Part 4: Synthesis and Structure—Activity Relationships for 1-(N-(Methyl)-N-(phenylsulfonyl)amino ]-2-(phenyl)-4-( 4(4-(N-(alkyl)-N-(benzyloxycarbonyl)amino )p-iperidin-1-yl) butanes," Bioorganic & Medicinal Chemistry Letters, 11:2475-79.
Gao et al., 1996, Molecular Cloning and Analysis of Functional Envelope Genes From Human Immunodeficiency Virus Type-1 Sequence Subtypes A through G, Journal of Virology, 70:1651-1667.
GenBank Accession No. AF324493, HIV-1 Vector pNL4-3, completed sequence, 2010.
Gerdes et al. 1990, "The Hok Killer Gene Family in Gram-negative Bacteria," The New Biologist: 2:946-56.
Grovit-Ferbas et al. 1998, "Potential Contribution of Viral Envelope and Host Genetic Factors In Human Immunodeficiency Virus Type 1-Infected Long Term Survivor" Journal of Virology, 72:8650-8658.
Helseth et al., 1990, "Rapid Complementation Assays Measuring Replicative Potential of Human Immunodeficiency Virus Type-1 Envelope Glycoprotein Mutants" Journal of Virology, 64:2416-2420.
Hertogs et al., 1998, "A Rapid Method for Simultaneous Detection of Phenotypic Resistance to Inhibitors of protease and Reverse Transcriptase in Recombinant Human Immunodeficiency Virus Type 1 Isolates from Patients Treated with Antiretroviral Drugs" Antimicrob. Agents Chemother. 42:269-76.
Hodgson et al., 2004, "Chemokines and Drug Discovery", Drug News Perspect., 17(5), 335-338.
Hioe, et al., 1997, "Resting Cell Neutralization Assay for HIV-1 Primary Isolates," Methods: A Companion to Methods in Enzymol. 12:300-305.
Hu et al., 2000, Evolution of the Human Immunodeficiency Virus Type 1 Envelope during Infection Reveals Molecular Corollaries of Specificity for Coreceptor Utilization and AIDS Pathogenesis, Journal of Virology, 74(24):11858-11872.
Hwang et al., 1997, "A Conditional Self-inactivating Retrovirus Vector That Uses a Tetracycline-responsive Expression System" Journal of Virology, 71: 7128-31.
Japour et al., 1993, "Standardized Peripheral Blood Mononuclear Cell Culture Assay for Determination of Drug Susceptibilities of Clinical Human Immunodeficiency Virus Type 1 Isolates," Antimicrob. Agents Chemo. 37:1095-01.
Judice et al., 1997, "Inhibition HIV Type 1 Infectivity by Constrained Alphahelical Peptides: Implications for the Viral Fusion Mechanism," Proc. Natl. Acad. Sci. US A. 94:13426-30.

(56) References Cited

OTHER PUBLICATIONS

Ketas et al., 2003, "Entry Inhibitors SCH-C, RANTES, and T-20 block HIV Type I Replication in Multiple Cell Types" AIDS Res Hum Retroviruses 19(3):177-86.
Kilby et al., 1998, "Potent Suppression of HIV-1 Replication in Humans by T-20, a Peptide Inhibitor of Gp41-mediated Virus Eutiy," Nat Med., 4:1302-07.
Kuritzkes, D.R. et al., 2004, "Antiretroviral activity of the anti-CD4 monoclonal antibody TNX-355 in patients infected with HIV type 1," J. Infect. Dis. 189:286-291.
Labrosse et al., 1997, "Resistance to a Drug Blocking Human Immunodeficiency Virus Type 1 Entry (RPR103611) is Conferred by Mutations in gp41" Journal of Virology, 71(11): 8230-8236.
Labrosse et al., 2003, "Baseline susceptibility of primary human immunodeficiency virus type 1 to entry inhibitors," J. Virol. 77(2):1610-1613.
Luciw P., 1996, "Incorporation of PR160gag-pol into Virions" Human Immunodeficiency Viruses and Their Replication, Chapter 60 in Fields Virology, ed. Fields et al.. Lippincott Williams and Wilkens, Philadelphia, p. 1927.
Mascola et al., 2000, "HIV-1 Entry at the Mucosal Surface: Role of Antibodies in Protection," AIDS, 14 (suppl3):S167-174.
Mascola et al., 2000, "Protection of Macaques Against Vaginal Transmission of a Pathogenic HIV-1/siv Chimeric Virus by passive Infusion of Neutralizing Antibodies" Nature Med 6:207-10.
Maxam, A. and Gilbert, W., "Sequencing End-Labeled DNA with Base-Specific Chemical Cleavages," 1980, In: Methods in Enzymology, Grossman, L. and Moldave, K., eds., 65:499-560.
Miyoshi et al, 1998, "Development of a Self-inactivating Lentivirus Vector." Journal of Virology, 72:8150-5 7.
Molecular Cloning :A Laboratory Manual, 2001, Sambrook, J. and Russell, D., eds., 3rd ed., Cold Spring Harbor Laboratory, NY.
Montefiori et al., 2001, "Neutralizing Antibodies Associated with Viremia Control in a Subset of Individuals after Treatment of Acute Human Immunodeliciency Virus Type 1 Infection" Journal of Virology, 75(21): 10200-10207.
Naviaux et al., 1996, "The Pcl Vector System: Rapid production of Helper-free, High-titer, Recombinant Retroviruses" Journal of Virology, 70: 5701-05.
Petropoulos et al., 2000, "A Novel- Phenotypic Drug Susceptibility Assay for HIV-1," Antimicrob. Agents & Chem., 44:920-28.
Pharmaceutical Research and Manufacturers of America. "New Medicines in Development for Aids" 1999.
Piketty et al., 1999, "Efficacy of a Five-drug Combination Including Ritonavir, Saquinavir and Efavirenz in Patients Who Failed on a Conventional Triple-drug Regimen: Phenotypic Resistance to protease Inhibitors predicts Outcome of Therapy," Aids 13:f71-f77.
Porter et al., 1998, Cationic Liposomes Enhance the Rate of Transduction by a Recombinant Retroviral Vector in Vitro and in Vivo, Journal of Virology, 12:4832-40.
Reimann et al., 1995, "In Vivo Administation of CD4-specific Monoclonal Antibody: Effect on provirus Load in Rhesus Monkeys Chronically Infected with the Simian Immunodeficiency Virus ofMacaques," Aids Res. Hum. Retroviruses, 11:517-25.
Rencher et al., 1995, "Does the Key to a Successful HIV Type 1 Vaccine Lie among the Envelope Sequences of Infected Individuals?" AIDS Research and Human Retroviruses 11(9):1131-1133.
Retroviruses, 1997, Coffin, J., Hughes, S., Varmus, H., eds., Cold Spring Harbor Laboratory Press, Cold Spring Harbor, NY.
Richman, 1998, "Nailing down Another HIV Target" Nature Med., 4:1232-1233.
Rimsky et al., 1998, "Determinants of Human Immunodeficiency Virus Type I Resistance to Gp41-derived Inhibitory Peptides" Journal of Virology, 72:986-93.
Rodriguez-Rosado et al., 1999, "Introduction of HIV Drug-resistance Testing in Clinical Practice," Aids, 13:1007-14.
Roehr, 2003, "New Anti-HIV Monoclonal Antibody Shows Promise in Humans", Medscape Medical News Feb. 12, 2003, http://www.medscape.com/viewarticle/449362.
Sanger et al., 1977, "DNA sequencing with chain-terminating inhibitors," Proc. Natl. Acad. Sci. USA, 74:5463-5467.
Sarkar et al., 1990, "The "Megaprimer" Method of Site-Directed Mutagenesis," Biotechniques, 8:404-07.
Sarkat et al., 1990, "Shedding Light onPCR contamination," Nature, 343:27.
Schinazi et al., 1999, "Mutations in Retroviral Genes Associated with Drug Resistance," Intl. Antiviral News, 7:46-49.
Schurman et al., 2004, "Antiviral Activity of a CCR5 Receptor Antagonist," Eleventh Conference on Retroviruses and Opportunistic Infections, abstract 140LB, San Francisco, CA.
Shi et al., 1997, "A Recombinant Retroviral System for Rapid In Vivo Analysis of Human Immunodeficiency Virus Type 1 Susceptibility to Reverse Transcriptase Inhibitors" Antimicrobrial Agents and Chemotherapy, 41:2781-85.
Si et al., 2004, Small-Molecule Inhibitors of HIV-1 Eutty Block Receptor-Induced Conformational Changes in the Viral Envelope Glycoproteins, Proc. Natl. Acad. Sci. U S A., 101(14):5036-5041.
Si et al, SuppText: Small-molecule inhibitors of HIV-1 entry block receptorinduced conformational changes in the viral envelope glycoprotein, PNAS, Apr. 6, 2004 (Apr. 6, 2004). pp. 1-2, XP055169026, Retrieved from the Internet: http://www.pnas.org/content/suppl/2004/03/17/0307953101.DC1/07953SuppText.html.
Sista et al., 2003, "Subgroup analysis of baseline (BL) susceptibility and early virological response to Enfuvirtide in the combined TORO studies," XII International HIV Drug Resistance Workshop, Cabo Del Sol, Los Cabos, Mexico, Poster No. 55.
Soriano,V. and Mendoza, C., "Genetic Mechanisms of Resistance to Protease Inhibitors and Entry Inhibitors," 2002, HIV Clin. Trials 3(3):249-257.
Stephenson, 1999, "New Class of Anti-HIV Drugs" JAMA, 282: 1994.
Strizki et al., 2005, "Discovery and Characterization of Vicriviroc (SCH 417690), a CCR5 Antagonist with Potent Activity against Human Immunodeficiency Virus Type 1",Antimicrobial Agents and Chemotherapy, vol. 49, No. 12,4911-4919.
Strizki et al., 2001, "SCH-C (SCH 351125), an orally bioavailable, small molecule antagonist of the chemokine receptor CCR5, is a potent inhibitor of HIV-1 infection in vitro and in vivo", PNAS, vol. 98, No. 22, 12718-12723.
Trkola et al., 1991, "A Cell Line-Based Neutralization Assay For Primary Human Immunodeficiency Virus Type-I Isolates That Use Either The CCR5 Or The CXCR4 Coreceptor" Journal of Virology, 73:8966-8974.
Wei et al., 2002, Emergence of Resistant Human Immunodeficiency Virus Type 1 ion Patients Receiving Fusion Inhibitor (T-20) Monotherapy, Antimicrob Agents Chemother., 46(6): 1896-1905.
WHO, Unaids/World Health Organization. Report: Aids Epidemic Update: Dec. 1999.
Wild et al., 1992, "A Synthetic Peptide Inhibitor of HIV Replication: Correlation Between Solution Structure and Viral Inhibition" Proc. Nat/. Acad. Sci. USA 89:10537-41.
Zennou et al., 1998, " Loss of Viral Fitness Associated with Multiple Gag and Gag-pol processing Defects in Human Immunodefiency Virus Type I Variants Selected for Resistance toProtease Inhibitors in vivo.", Journal of Virology, 72:3300-06.
Zhange et al., 1999, "Primary Virus Envelope Cross-Reactivity of the Broadening Neutralizing Antibody Response During Early Chronic Human Immunodeficiency Virus Type I Infection" Journal of Virology, 73(6): 5225-5230.
Ziermann et al., 2000, "A Mutation in HIV-1 Protease, N88s, That Causes in Vitro Hypersensitivity to Amprenavir," Journal of Virology, 74:4414-19.
U.S. Appl. No. 11/146,879 , Notice of Allowance, dated Aug. 8, 2013, 40 pages.
U.S. Appl. No. 11/146,879 , Office Action, dated May 4, 2012, 14 pages.
U.S. Appl. No. 11/146,879 , "Office Action", dated Jan. 2, 2013, 15 pages.
EP 11161793.2 , Extended European Search Report, dated Oct. 23, 2015, 13 pages.
EP 11161793.2 , Office Action, dated Feb. 22, 2017, 4 pages.

(56) References Cited

OTHER PUBLICATIONS

EP 11161793.2 , Notice of Decision to Grant, dated Sep. 13, 2018, 2 pages.
EP 11161793.2 , Office Action, dated Nov. 15, 2017, 3 pages.
EP 18199100.1 , Extended European Search Report, dated Mar. 29, 2019, 12 pages.
EP 791 148.9, Communication pursuant to Rule 71(3) EPC indicating intention to grant European patent dated Oct. 26, 2011.
EP 05 791 148.9, Office Action, dated Jun. 1, 2010.
EP 11161793, Partial European Search Report, dated Feb. 23, 2015.
PCT/US03/04373, International Search Report, dated Jul. 22, 2003.
PCT/US2005/20240, International Search Report, dated Jan. 3, 2006.

\* cited by examiner

PhenoSense HIV Entry Assay

Envelope Expression Vector: pHIVenv

HIV-1 Expression Vector: pHIVluc ΔU3

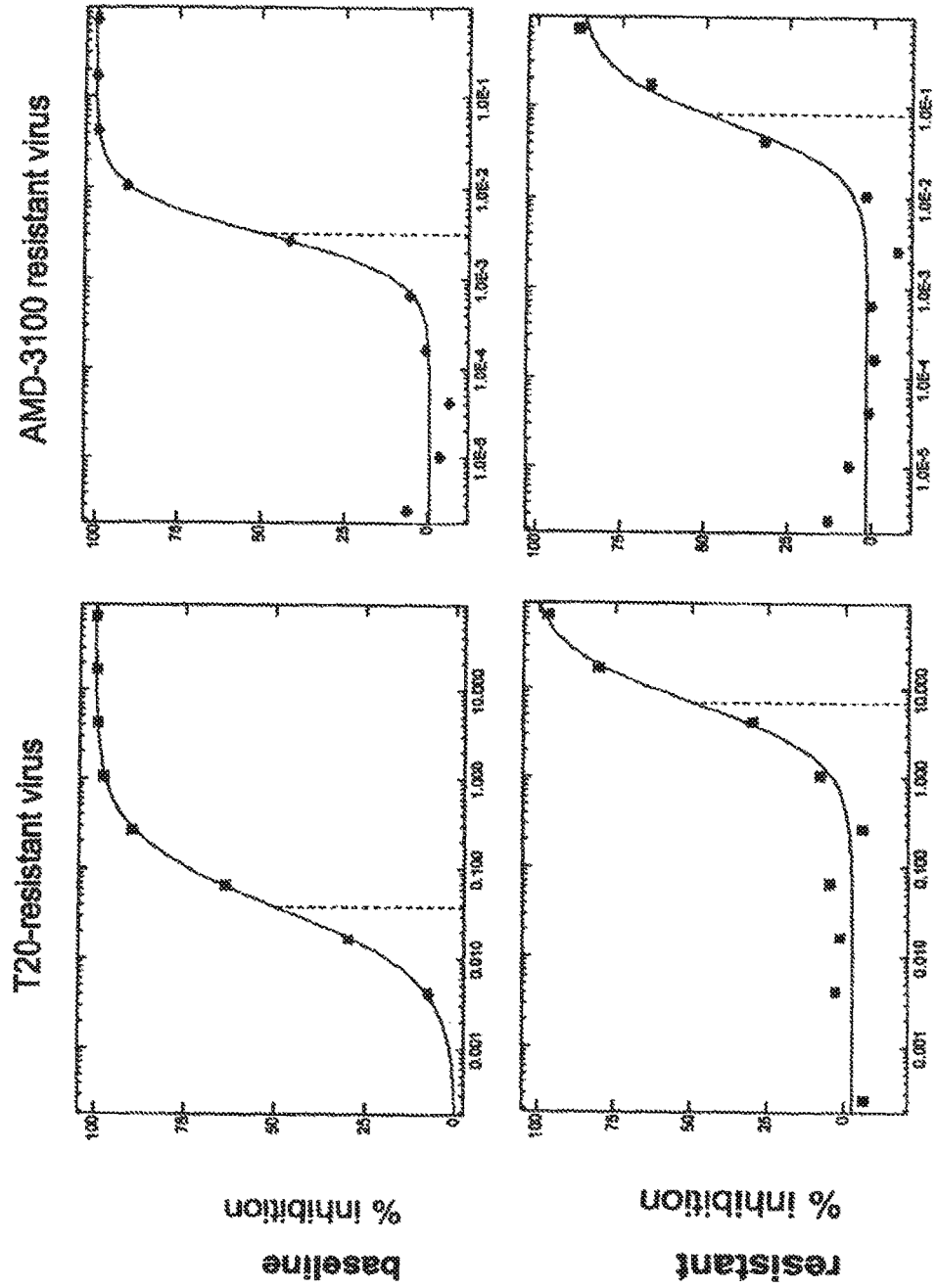
Fig. 5 Entry Inhibitor Resistance I: viruses with increased IC50

Fig. 6

Detection of Resistant Variants:
DNA Mixing Experiments

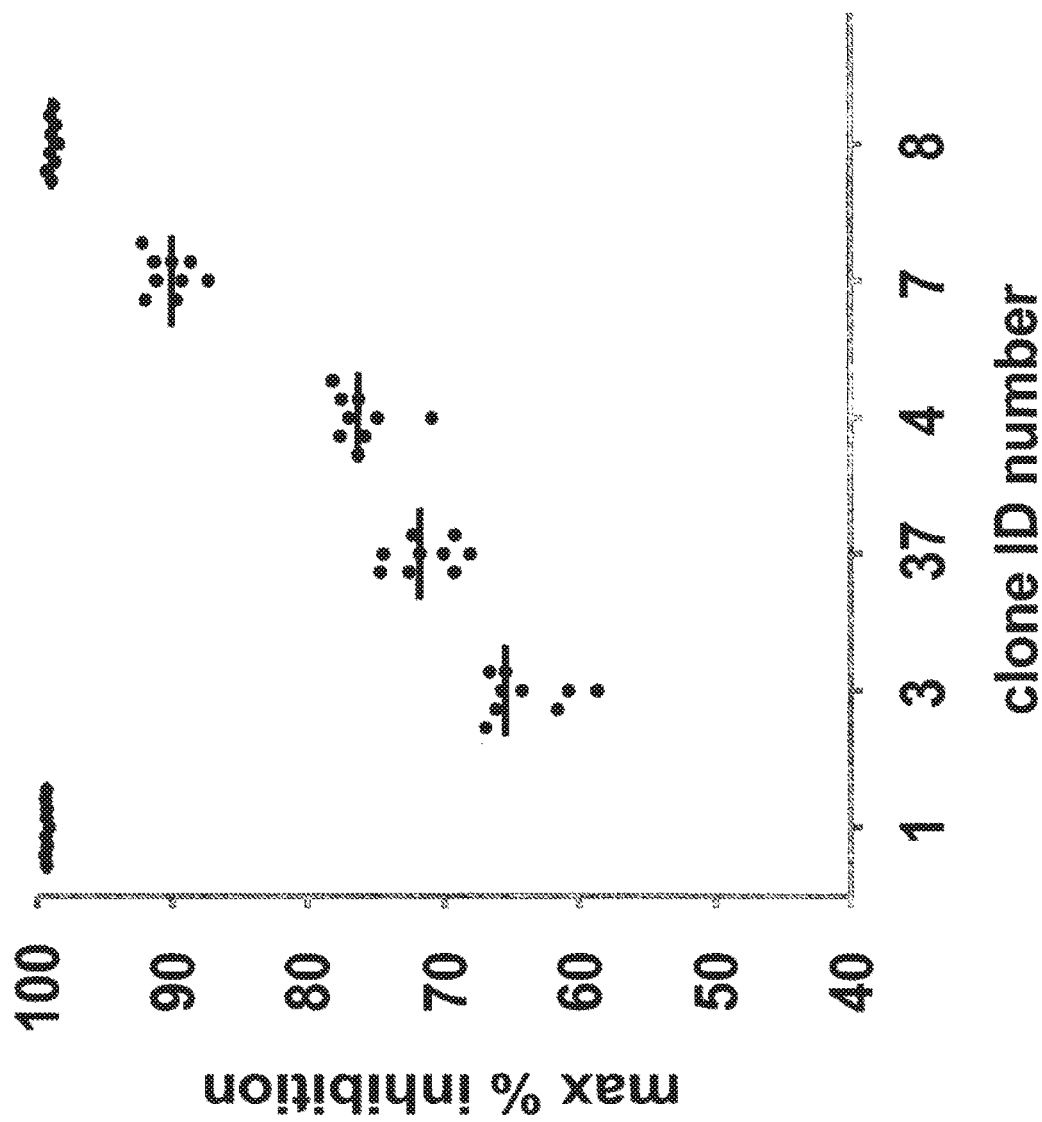

SEQUENCE LISTING

<160> NUMBER OF SEQ ID NOS: 10

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1
ggagcattta caagcagcaa cacagc                                          26

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

```
<400> SEQUENCE: 2
ttccagtcav acctcaggta c                                       21

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
agaccaatga cttayaagg                                          19

<210> SEQ ID NO 4
<211> LENGTH: 35
<212> TYPE: DNA
<213> ORGANISM: Artificial Sequence
<220> FEATURE:
<223> OTHER INFORMATION: Synthetic Construct

<400> SEQUENCE: 4
gggctcgaga ccggtcagtg gcaatgagag tgaag                        35

<210> SEQ ID NO 5
<211> LENGTH: 37
<212> TYPE: DNA
<213> ORGANISM: Artificial Sequence
<220> FEATURE:
<223> OTHER INFORMATION: Synthetic Construct

<400> SEQUENCE: 5
gggctcgaga ccggtgagca gaagacagtg gcaatga                      37

<210> SEQ ID NO 6
<211> LENGTH: 36
<212> TYPE: DNA
<213> ORGANISM: Artificial Sequence
<220> FEATURE:
<223> OTHER INFORMATION: Synthetic Construct

<400> SEQUENCE: 6
gggctcgaga ccggtgagca gaagacagtg gcaatg                       36

<210> SEQ ID NO 7
<211> LENGTH: 35
<212> TYPE: DNA
<213> ORGANISM: Artificial Sequence
<220> FEATURE:
<223> OTHER INFORMATION: Synthetic Construct

<400> SEQUENCE: 7
gggtctagaa cgcgttgcca cccatcttat agcaa                        35

<210> SEQ ID NO 8
<211> LENGTH: 38
<212> TYPE: DNA
<213> ORGANISM: Artificial Sequence
<220> FEATURE:
<223> OTHER INFORMATION: Synthetic Construct

<400> SEQUENCE: 8
gggtctagaa cgcgtccact tgccacccat bttatagc                     38

<210> SEQ ID NO 9
<211> LENGTH: 33
```

```
<212> TYPE: DNA
<213> ORGANISM: Artificial Sequence
<220> FEATURE:
<223> OTHER INFORMATION: Synthetic Construct

<400> SEQUENCE: 9
gggtctagaa cgcgtccact tgccacccat btt                          33

<210> SEQ ID NO 10
<211> LENGTH: 38
<212> TYPE: DNA
<213> ORGANISM: Artificial Sequence
<220> FEATURE:
<223> OTHER INFORMATION: Synthetic Construct

<400> SEQUENCE: 10
gatggtctaa gacgctgttc aatatccctg cctaactc                     38
```

COMPOSITIONS AND METHODS FOR DETERMINING RESISTANCE TO INHIBITORS OF VIRUS ENTRY USING RECOMBINANT VIRUS ASSAYS

1. CROSS-REFERENCE TO RELATED APPLICATION AND STATEMENT OF POTENTIAL GOVERNMENT RIGHTS

The present application is a continuation of U.S. patent application Ser. No. 14/100,467, filed Dec. 9, 2013, which is a continuation of U.S. patent application Ser. No. 11/146,879, filed Jun. 6, 2005, which issued as U.S. Pat. No. 8,603,736 on Dec. 10, 2013, which is entitled to and claims benefit of U.S. Provisional Application No. 60/577,851, filed Jun. 7, 2004. Each of these applications is hereby incorporated by reference in its entirety.

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

The invention described in this application was supported, in part, by Small Business Innovation Research (SBIR) Grant R44 AI048990. The United States government may have certain rights to this invention.

2. BACKGROUND

Enveloped animal viruses attach to and enter the host cell via the interaction of viral proteins in the virion membrane (envelope proteins) and cell surface proteins (virus receptors). Receptor recognition and binding are mediated by the surface envelope protein. Virus entry is an attractive target for anti-viral treatment; numerous drugs that are designed to block virus attachment or membrane fusion have been or are currently being evaluated in preclinical or clinical studies (Richman, 1998; PhRMA, 1999; Stephenson, 1999). For example, the attachment inhibitor SCH-D, which blocks the interaction between viral membrane proteins and CCR5 is currently being evaluated in clinical studies for its effectiveness as an anti-viral treatment (Schurmann, D. et al., 2004). Other entry inhibitors currently under investigation include UK-427857 (Pfizer), TNX-355 (Tanox Inc.), AMD-070 (AnorMED), Pro 140 (Progenics), FP-21399 (EMD Lexigen), BMS-488043 (Bristol-Myers Squibb), and GSK-873,140 (GlaxoSmithKline). One entry inhibitor, T-20 (Roche/Trimeris), has been approved to treat HIV infection.

As these drugs continue to be developed and enter the clinic, assays are needed that can rapidly and easily detect the emergence of viruses with reduced susceptibility to entry inhibitors. In particular, methods for determining whether an HIV is resistant to an entry inhibitor, e.g., SCH-C, SCH-D, UK-427857 and/or TNX-355, are needed. These and other unmet needs are provided by the present invention.

3. SUMMARY

In certain aspects, the invention provides a method for determining whether an human immunodeficiency virus ("HIV") is resistant to an HIV entry inhibitor. In one aspect, the invention provides a method for determining whether an human immunodeficiency virus ("HIV") is resistant to an HIV entry inhibitor that comprises generating a log-sigmoid inhibition curve comprising data points that measure entry of the HIV into a cell in the presence of varying concentrations of the HIV entry inhibitor; and comparing the inhibition curve of step (a) to a log-sigmoid inhibition curve for a reference HIV. In certain embodiments, the curve for the reference virus at or near the same time as the log-sigmoid curve of the HIV. In certain embodiments, the curve for the reference virus can be a known, standard curve for the reference virus. In certain embodiments, a decrease in the maximum inhibition percentage observed for the HIV relative to that observed for the reference HIV indicates that the HIV is resistant to the HIV entry inhibitor. In certain embodiments, the entry inhibitor is selected from the group consisting of SCH-C, SCH-D, UK-427857, and TNX-355. In certain embodiments, the reference HIV is HXB2, NL4-3, or SF2. In certain embodiments, the HIV is from a subject infected with HIV.

In certain embodiments, the data points that measure entry of the HIV into the cell are determined by contacting an HIV viral particle with the cell in the presence of the HIV entry inhibitor, wherein the cell expresses a cell surface receptor to which the viral particle binds, and wherein the viral particle comprises: (i) a viral expression vector that lacks a nucleic acid encoding a functional viral envelope protein, but which comprises an indicator nucleic acid that produces a detectable signal when introduced into the cell, and (ii) a viral envelope protein encoded by a nucleic acid of the HIV; and measuring the amount of the detectable signal produced by the cell. In certain embodiments, the detectable signal is a fluorescent signal. In certain embodiments, the indicator nucleic acid encodes luciferase. In certain embodiments, the viral particle is produced by co-transfecting into a cell (i) a nucleic acid encoding a viral envelope protein of the HIV, and (ii) a viral expression vector lacking a nucleic acid encoding an envelope protein, wherein the vector comprises an indicator nucleic acid that produces a detectable signal. In certain embodiments, the cell surface receptor is CD4. In certain embodiments, the cell also expresses a chemokine receptor. In certain embodiments, the chemokine receptor is CXCR4 or CCR5. In certain embodiments, the HIV nucleic acid encodes gp160, gp120, and/or gp41.

In other aspects, the invention provides a method for determining whether an HIV population is resistant to an HIV entry inhibitor, wherein the method comprises generating a log-sigmoid inhibition curve comprising data points that measure entry of the HIV population into a cell in the presence of varying concentrations of the HIV entry inhibitor; and comparing the inhibition curve of step (a) to a log-sigmoid inhibition curve for a reference HIV population. In certain embodiments, a decrease in the maximum inhibition percentage observed for the HIV population relative to that observed for the reference HIV population indicates that the HIV is resistant to the HIV entry inhibitor.

In other aspects, the invention provides a method for determining whether an HIV is resistant to an HIV entry inhibitor that comprises determining a log-sigmoid inhibition curve comprising data points for entry of the HIV in the presence of varying concentrations of the HIV entry inhibitor, wherein if the entry of the HIV cannot be completely inhibited by the HIV entry inhibitor, the HIV is resistant to the HIV entry inhibitor.

In another aspect, the invention provides a method for determining whether an HIV population is resistant to an HIV entry inhibitor, comprising determining a log-sigmoid inhibition curve comprising data points for entry of the HIV population in the presence of varying concentrations of the HIV entry inhibitor, wherein if the entry of the HIV population cannot be completely inhibited by the HIV entry inhibitor, the HIV population is resistant to the HIV entry inhibitor.

4. BRIEF DESCRIPTION OF THE FIGURES

FIG. 1A: Structure of envelope expression and viral expression vectors.

The HIV envelope expression vector (pHIVenv) is modified to accept envelope sequences that have been amplified from subject plasma samples. The designations a/b and c/d, refer to restriction endonuclease sites positioned at the 5' and 3' end of the HIV-1 envelope polyprotein (gp160). The HIV expression vector (pHIVlucΔU3) encodes all HIV proteins except the envelope polyprotein. A portion of the envelope gene has been deleted to accommodate a indicator gene cassette, in this case, firefly luciferase that is used to monitor the ability of the virus to replicate in the presence or absence of anti-viral drugs. The 3' U3 region has been partially deleted to prevent transcription from the 5' LTR in infected cells. Virus produced in this system is limited to a single round of replication.

Figure 1B:
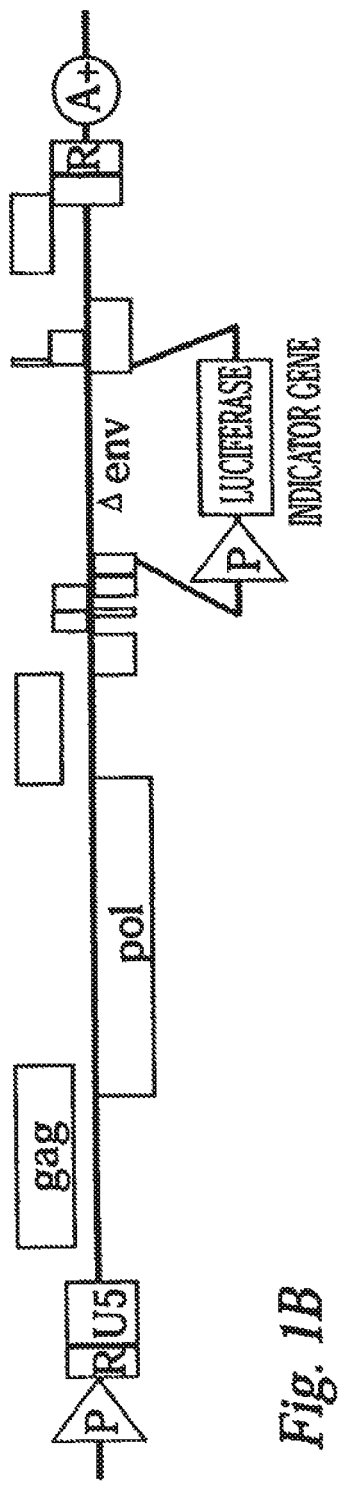

FIG. 1B: Cell Based Entry Assay

Drug susceptibility, co-receptor tropism and virus neutralization testing are performed by co-transfecting a host cell with pHIVenv and pHIVlucΔU3. The host cell produces HIV particles that are pseudo-typed with HIV envelope sequences derived from the test virus or subject sample. Virus particles are collected (.about.48 h) after transfection and are used to infect target cells that express HIV receptors (e.g. CD4) and co-receptors (e.g. CXCR4, CCR5). After infection (.about.72 h) the target cells are lysed and luciferase activity is measured. HIV must complete one round of replication to successfully infect the target host cell and produce luciferase activity. If the virus is unable to enter the target cell, luciferase activity is diminished. This system can be used to evaluate susceptibility to entry inhibitors, receptor and co-receptor tropism, and virus neutralization.

Figure 2:
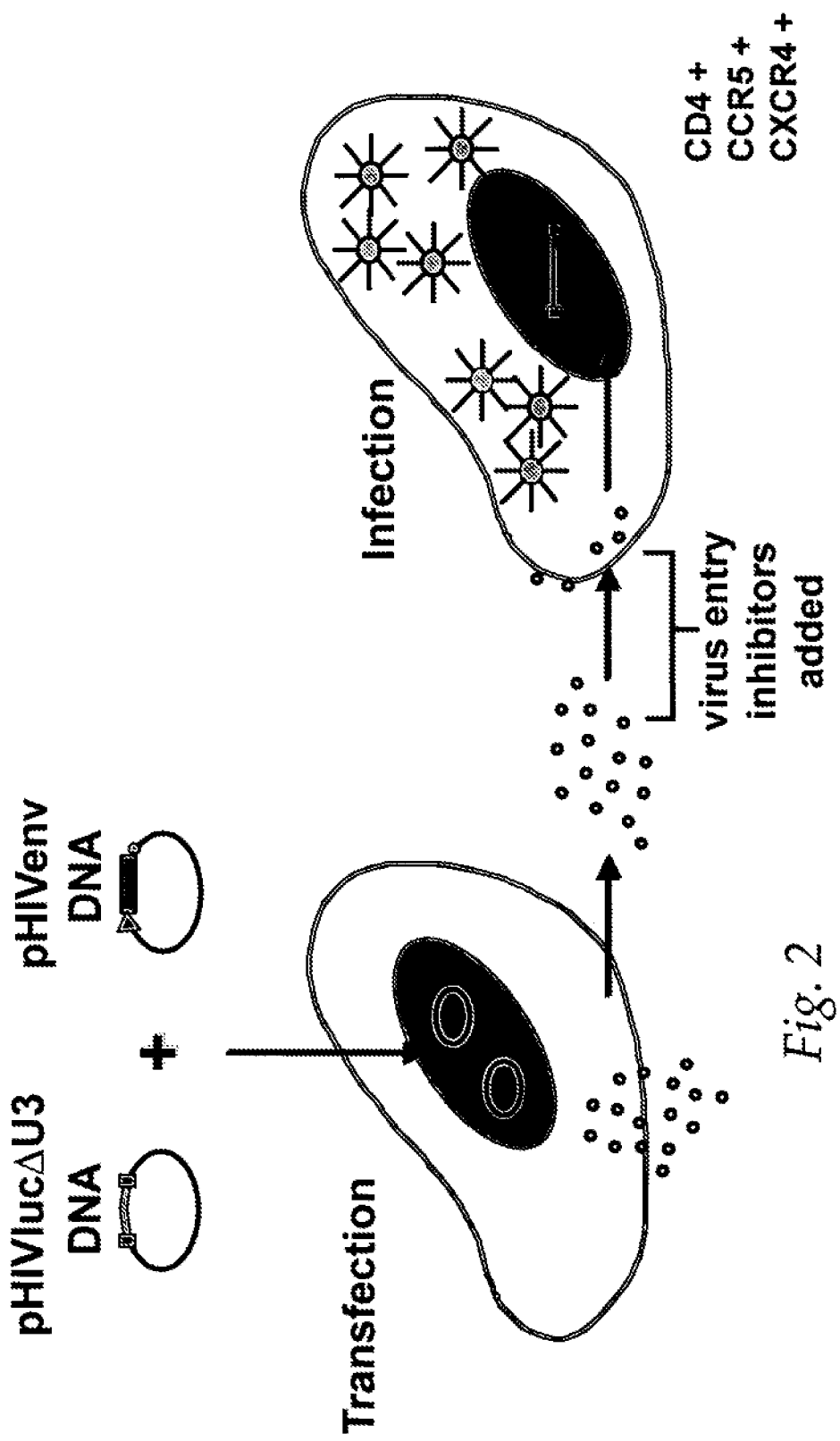
Figure 2:
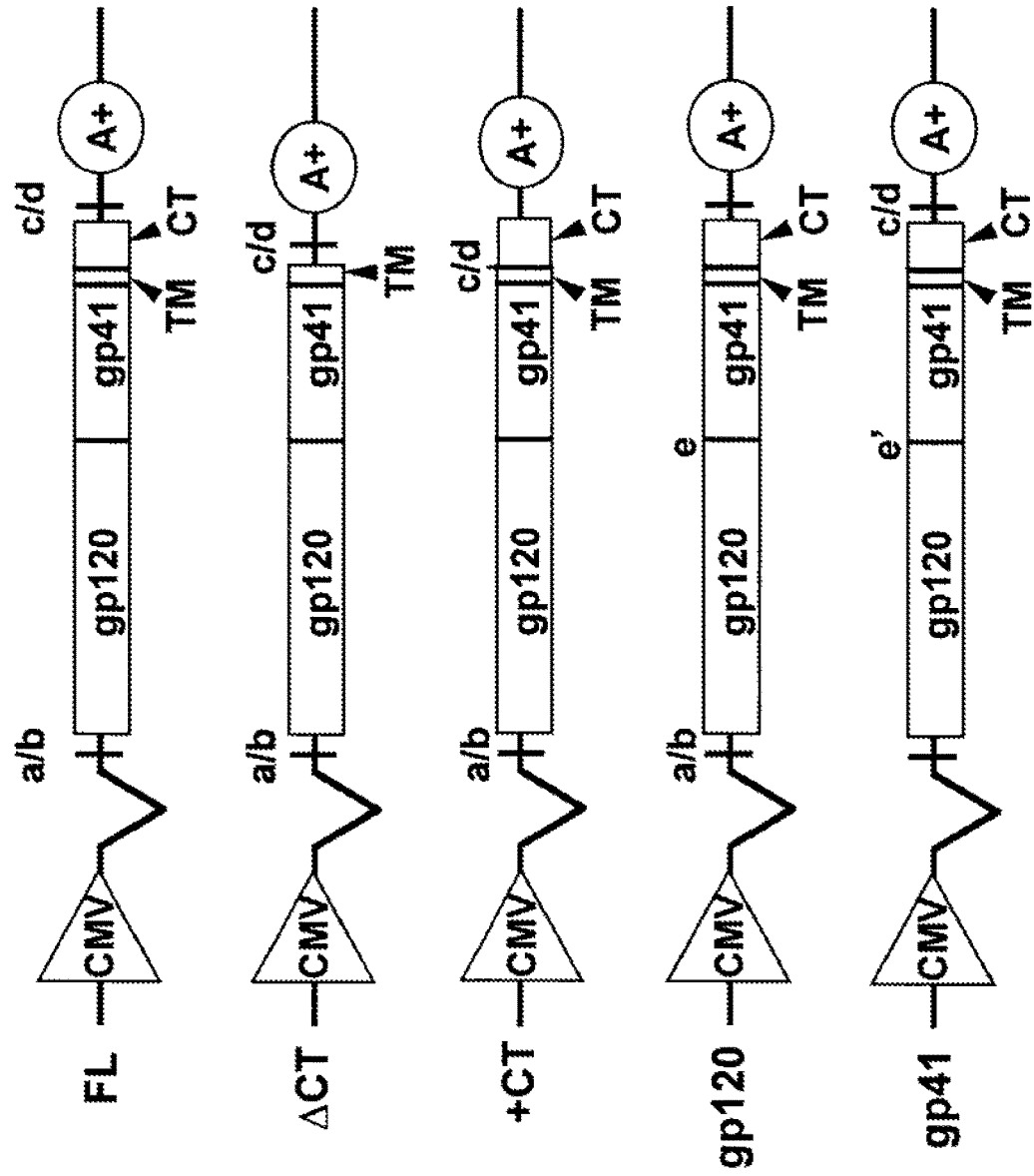

FIG. 2: HIV envelope expression vectors.

HIV envelope sequences are amplified from subject samples and inserted into expression vectors using restriction endonuclease sites (5' a/b and 3'c/d). Envelope transcription is driven by the immediate early gene promoter of human cytomegalovirus (CMV). Envelope RNA is polyadenylated using an simian virus 40 (SV40) polyadenylation signal sequence (A+). An intron located between the CMV promoter and the HIV envelope sequences is designed to increase envelope mRNA levels in transfected cells. FL-express full-length envelope proteins (gp120, gp41); ΔCT-express envelope proteins (gp120, gp41) lacking the C-terminal cytoplasmic tail domain of gp41; +CT-express envelope proteins (gp120, gp41) containing a constant pre-defined gp41 cytoplasmic tail domain; gp120-express gp120 proteins derived from the subject together with a constant pre-defined gp41; and gp41-express a constant pre-defined gp120 together with gp41 proteins derived from the subject.

Figure 3A:
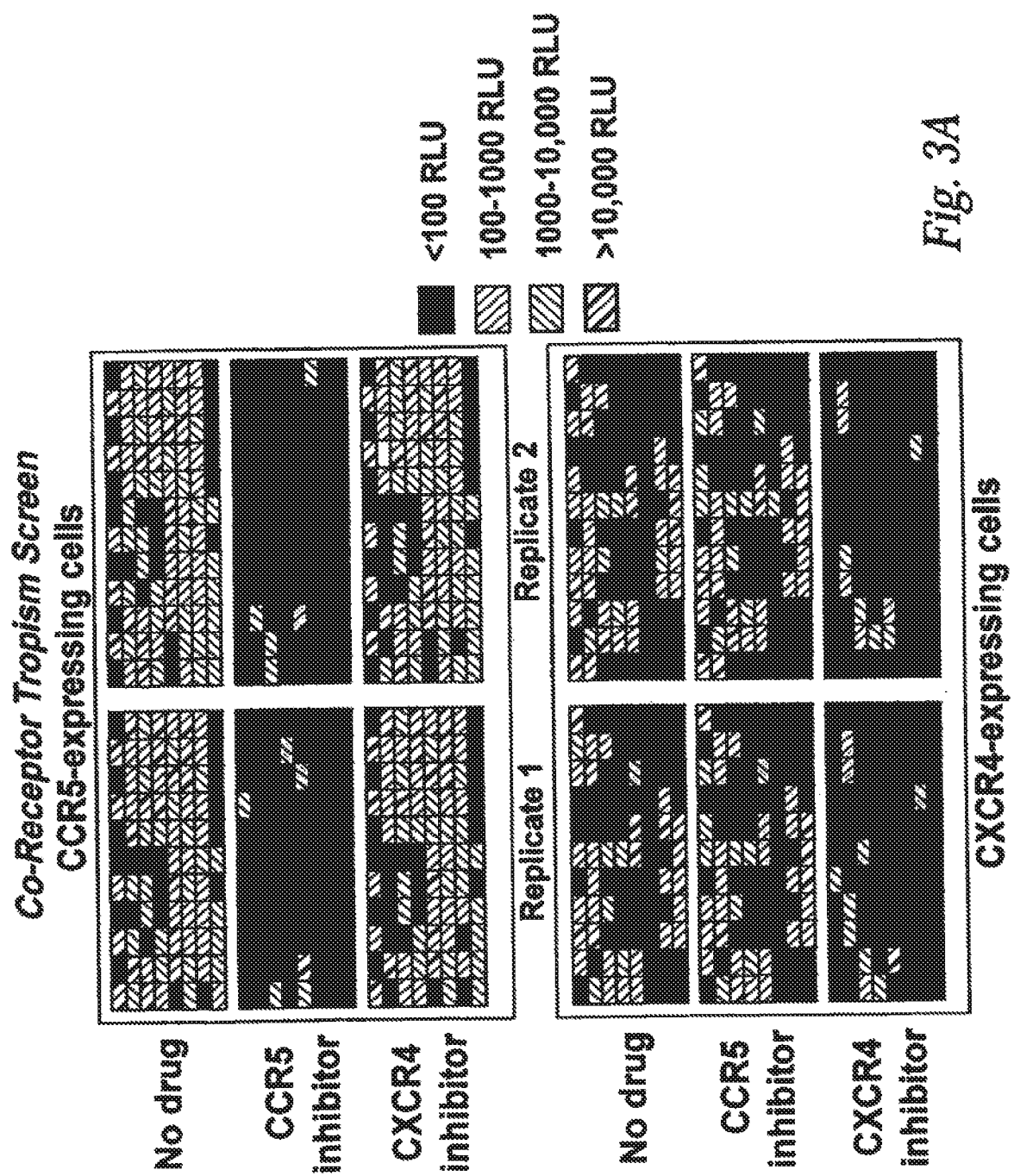

FIG. 3A: Co-receptor Tropism Screening Assay.

In this figure, the assay is performed using two cell lines. One cell line expresses CD4 and CCR5 (top six panels). The other cell line expresses CD4 and CXCR4 (bottom six panels). The assay is performed by infecting cells with a large number of recombinant virus stocks derived from cells transfected with pHIVenv and pHIVlucΔU3 vectors. The example shown represents the analysis of 96 viruses formatted in a 96 well plate. Infections are performed in the absence of drug (no drug), or in the presence of a drug that preferentially inhibits either R5 tropic (CCR inhibitor) or X4 tropic (CXCR4 inhibitor) viruses. Co-receptor tropism is assessed by comparing the amount of luciferase activity produced in each cell type, both in the presence and absence of drug (see FIG. 3B for interpretation of assay results).

Figure 3B:
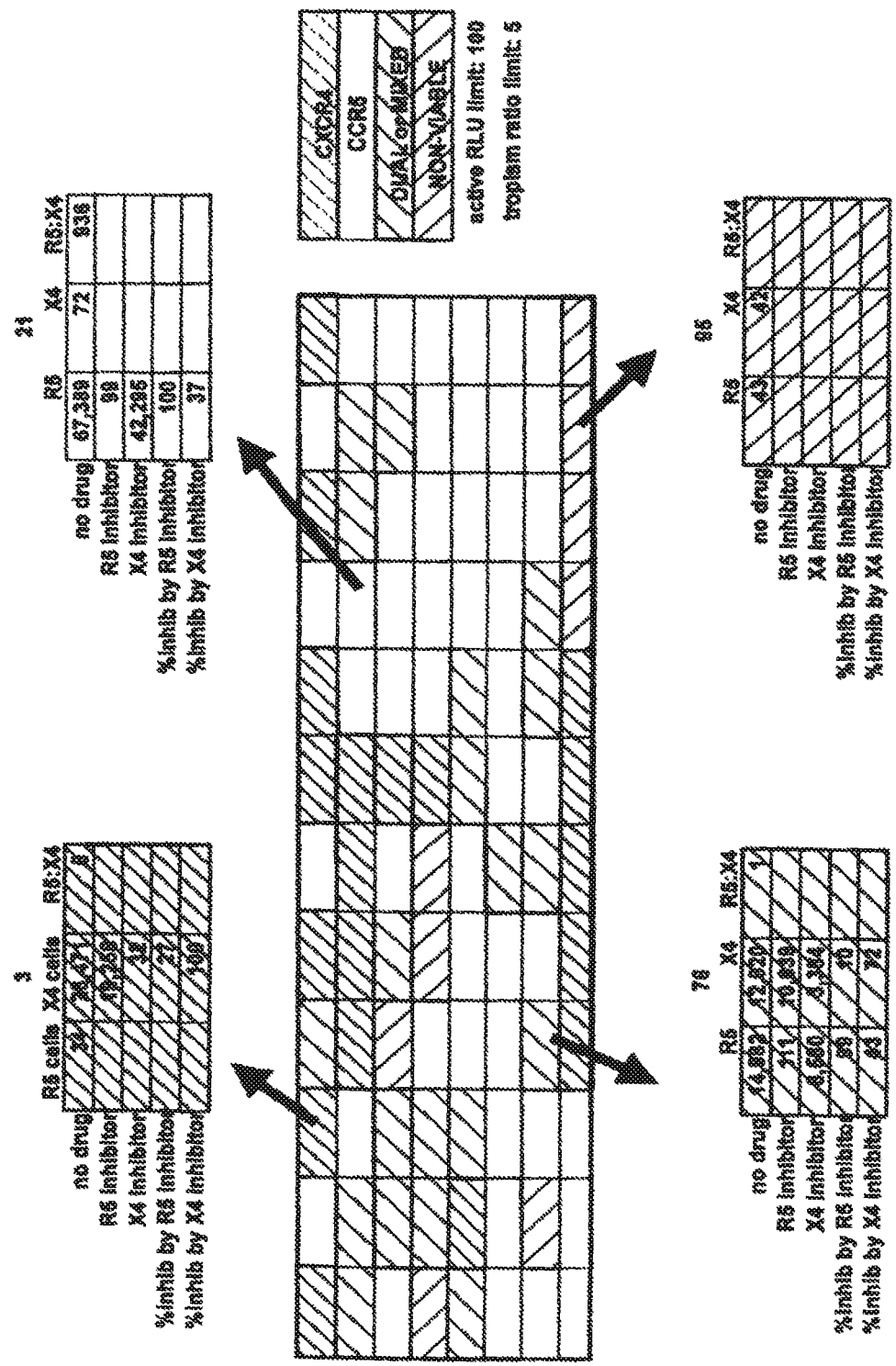

FIG. 3B: Determining co-receptor tropism.

In this figure, the results of the assay are interpreted by comparing the ability of each sample virus to infect (produce luciferase activity) cells expressing CD4/CCR5 (R5 cells) or cells expressing CD4/CXCR4 (X4 cells). The ability of a CCR5 or CXCR4 inhibitor to specifically block infection (inhibit luciferase activity) is also evaluated. X4 tropic viruses (green panels)—infect cells expressing CXCR4 but not cells expressing CCR5. Infection of X4 cells is blocked by the CXCR4 inhibitor. R5 tropic viruses (blue panels)-infect R5 cells but not X4 cells. Infection of R5 cells is blocked by the CCR5 inhibitor. Dual tropic or X4/R5 mixtures (yellow panels)infect X4 and R5 cells. Infection of R5 cells is blocked by the CCR5 inhibitor and infection of X4 cells is blocked by the CXCR4 inhibitor. Non-viable viruses (red panels)—do not replicate in either X4 or R5 cells.

Figure 4A:
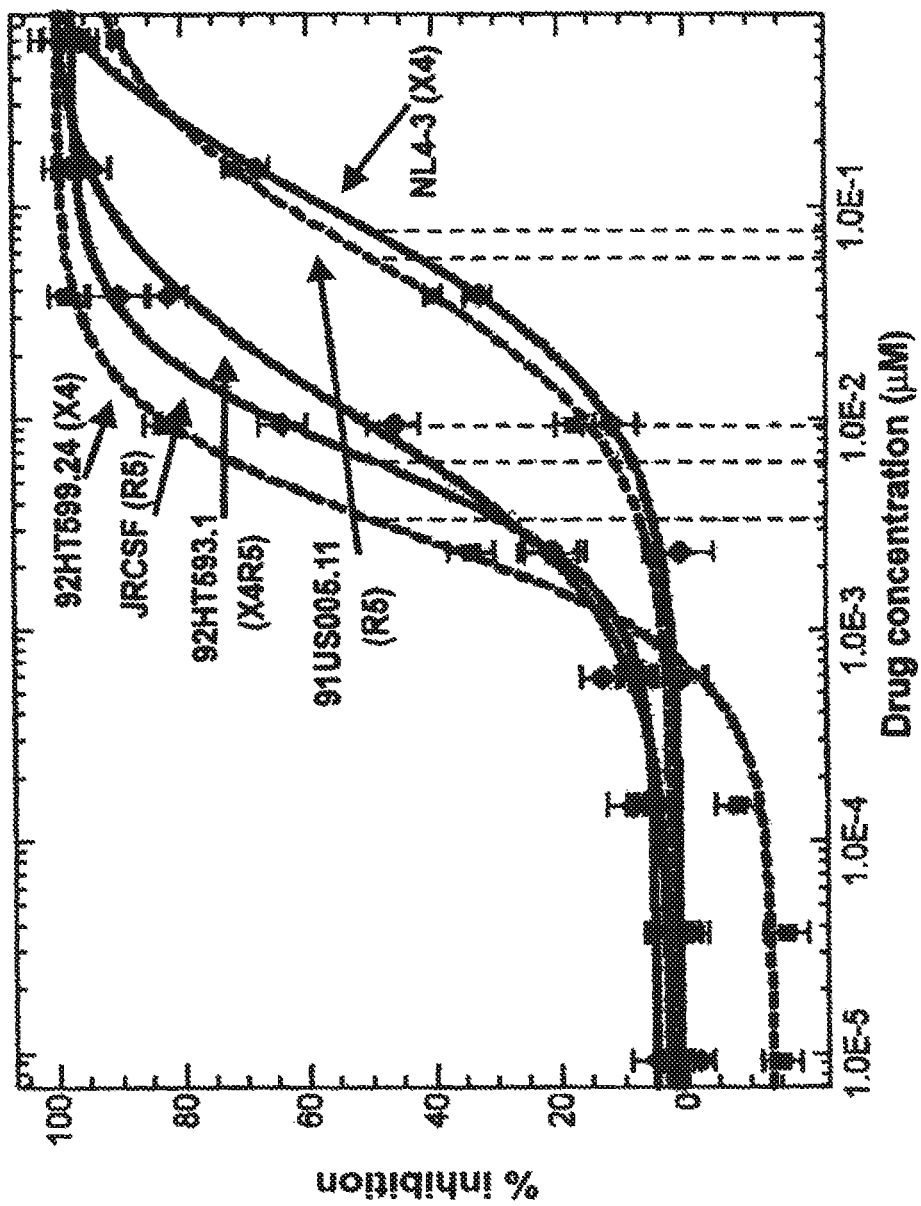

FIG. 4A: Measuring Entry Inhibitor susceptibility: Fusion Inhibitor.

In this figure, susceptibility to the fusion inhibitor T-20 is demonstrated. Cells expressing CD4, CCR5 and CXCR4 were infected in the absence of T-20 and over a wide range of T-20 concentrations α-axis log 10 scale). The percent inhibition of viral replication (y-axis) was determined by comparing the amount of luciferase produced in infected cells in the presence of T-20 to the amount of luciferase produced in the absence of T-20. R5 tropic, X4 tropic and dual tropic viruses were tested. Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. NL4-3: well-characterized X4 tropic strain; JRCSF: well-characterized R5 tropic strain; 91US005.11: R5 tropic isolate obtained from the NIH AIDS Research and Reference Reagent Program (ARRRP); 92HT593.1: Dual tropic (X4R5) isolate obtained from the NIH ARRRP; and 92HT599.24: X4 tropic isolate obtained from the NIH ARRRP.

Figure 4B:
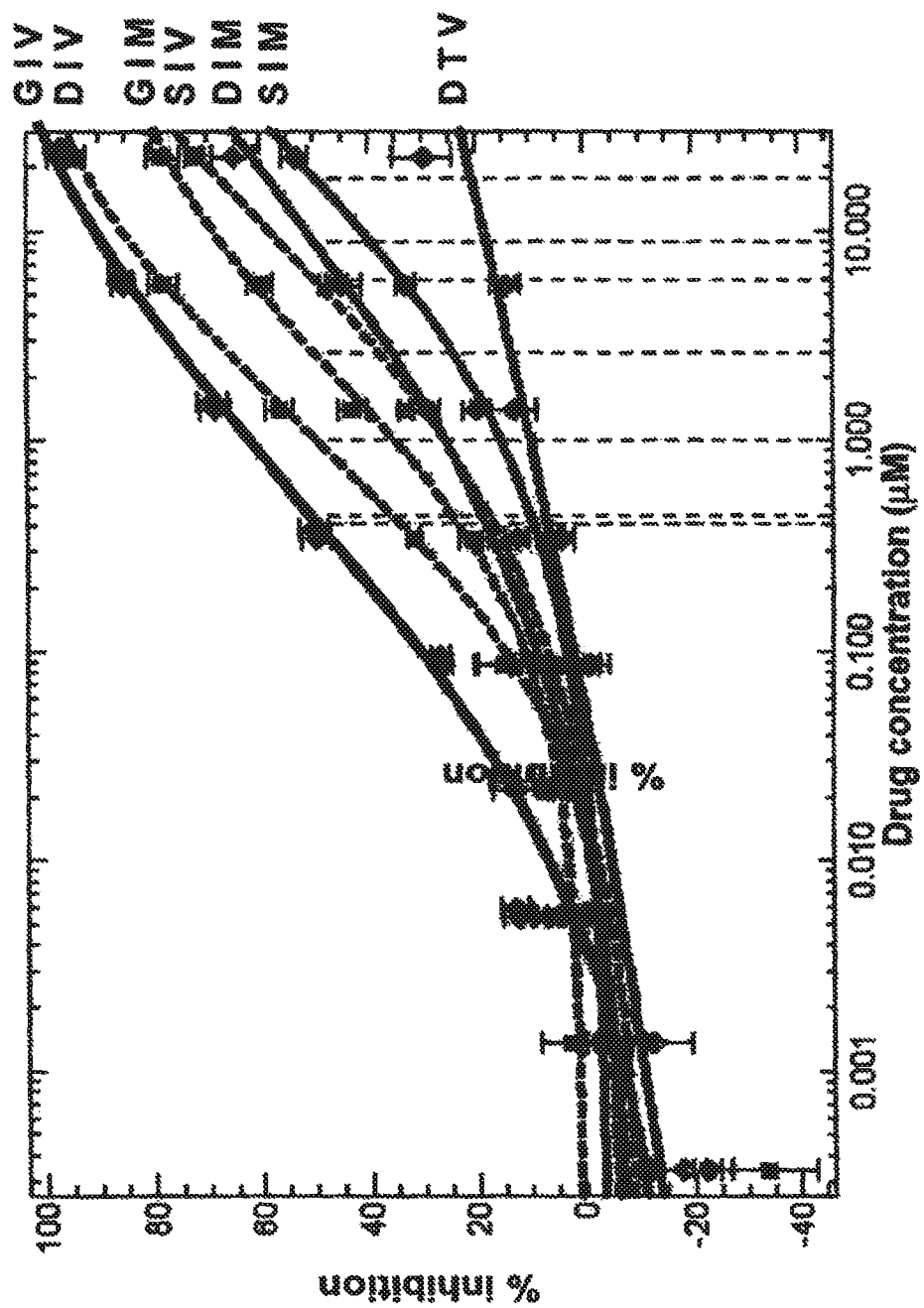

FIG. 4B: Measuring Entry Inhibitor susceptibility: Drug Resistance Mutations.

In this figure, reduced susceptibility to the fusion inhibitor T-20 conferred by specific drug resistance mutations in the gp41 envelope protein is demonstrated. Cells expressing CD4, CCR5 and CXCR4 were infected in the absence of T-20 and over a wide range of T-20 concentrations (x-axis log 10 scale). The percent inhibition of viral replication (y-axis) was determined by comparing the amount of luciferase produced in infected cells in the presence of T-20 to the amount of luciferase produced in the absence of T-20. Isogenic viruses containing one or two specific mutations in the gp41 transmembrane envelope protein were tested (highlighted in red in the figure legend). Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. No mutation (wildtype sequence): GIV; Single mutations: DIV, DIM, SIV; Double mutations: DIM, SIM, DTV.

FIG. 5: Competitive entry inhibitor resistance.

FIG. 5 demonstrates log-sigmoid curves for viruses resistant to AMD-3100 and T20, indicating that resistance to these entry inhibitors manifests as an increased $IC_{50}$ and that entry can be completely inhibited with high concentrations of inhibitor.

Figure 6:
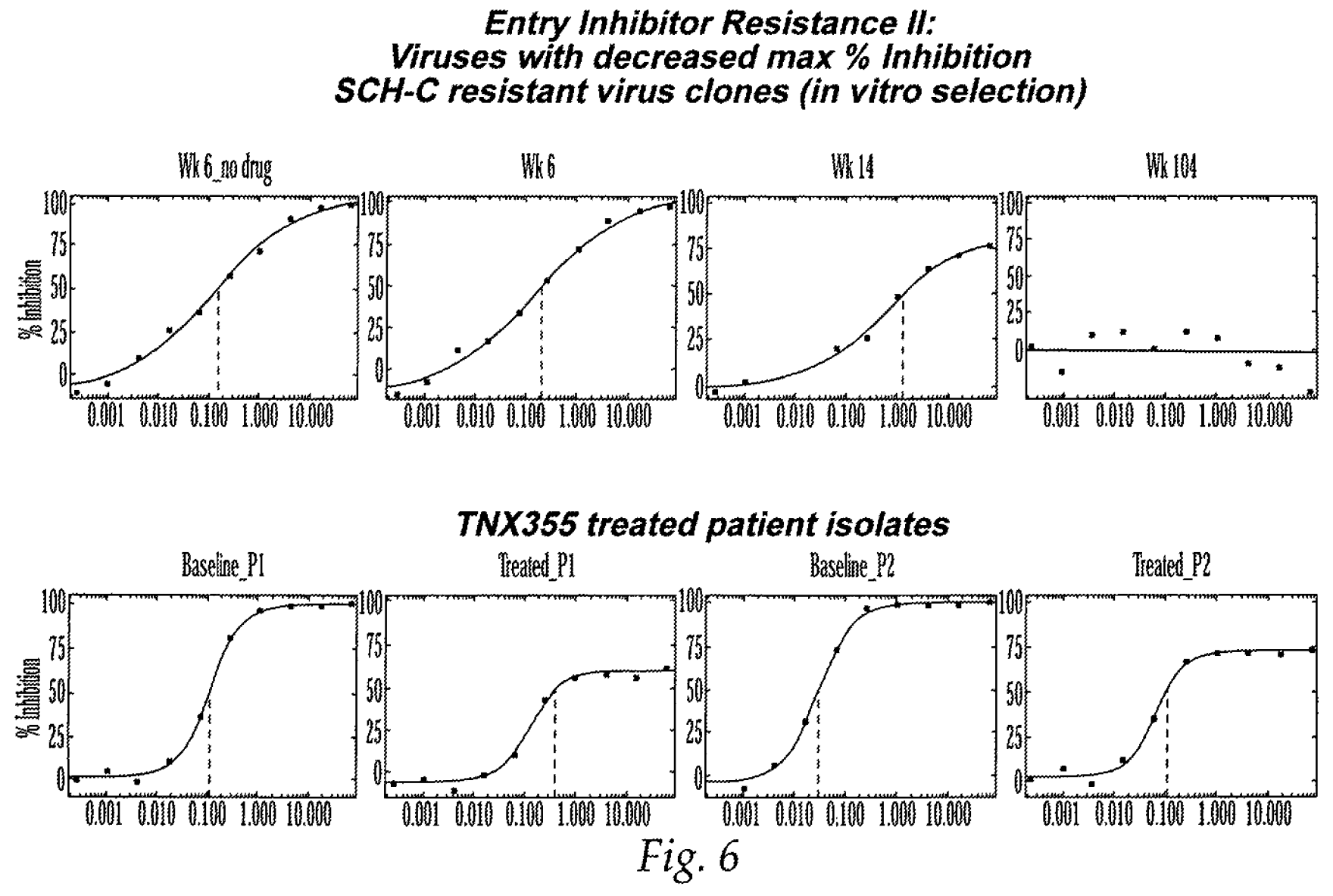

FIG. 6: Non-competitive entry inhibitor resistance.

FIG. 6 demonstrates log-sigmoid curves for viruses resistant to SCH-C and TNX-355, indicating that resistance to these entry inhibitors manifests as a reduced maximum percentage of inhibition.

Figure 7:
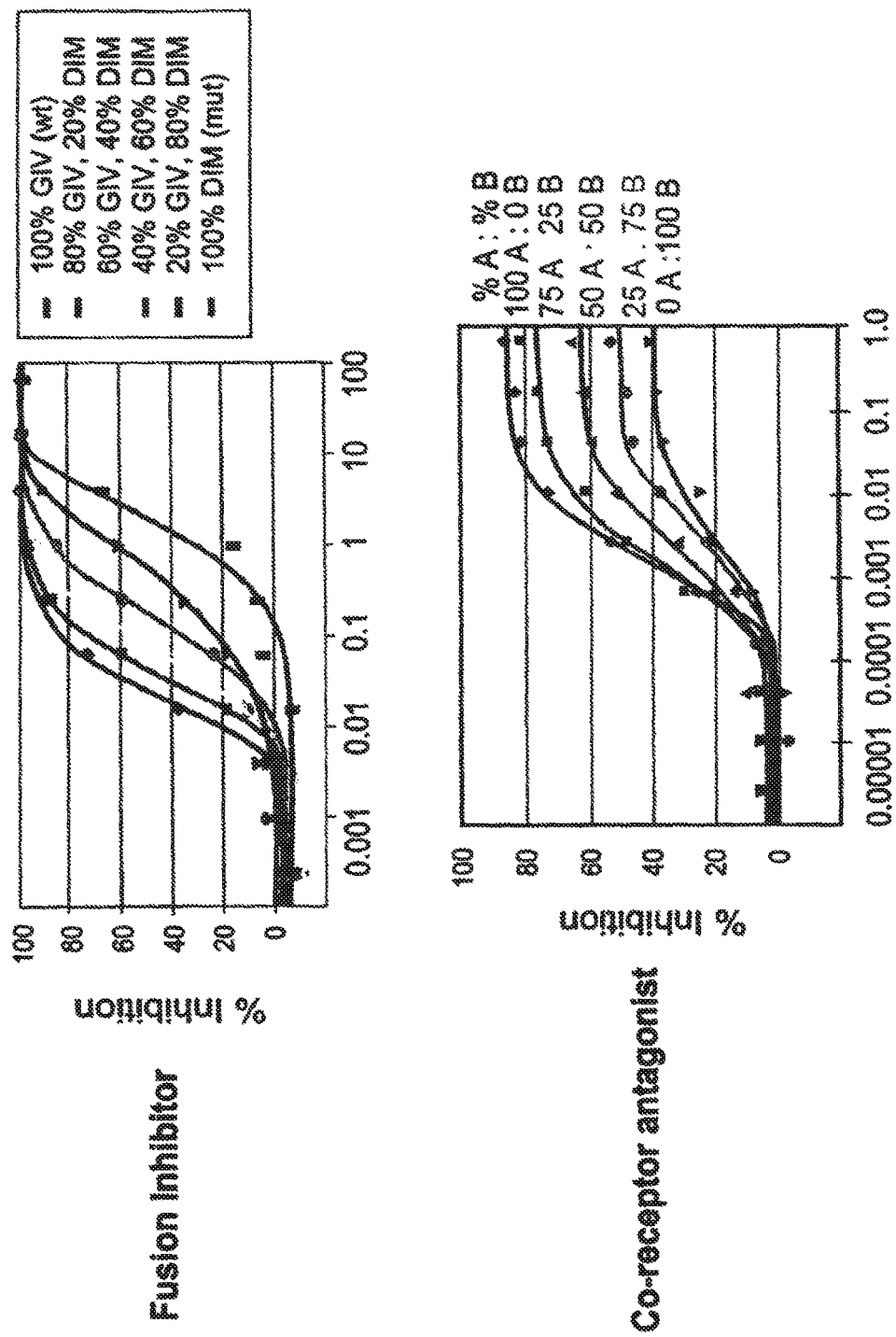

FIG. 7: Mixed susceptible and resistant viral envelope proteins.

FIG. 7 presents the results of DNA mixing experiments that demonstrate log-sigmoid curves for mixed resistant and sensitive envelope proteins. Briefly, the proportion of resistant and sensitive envelope proteins were varied as presented in the legend of the figures and the percentage inhibition observed was plotted against log 10 of inhibitor concentration. The results indicate that susceptibility or resistance of mixed populations of viruses to entry inhibitors can also be assessed according to the present invention.

Figure 8:
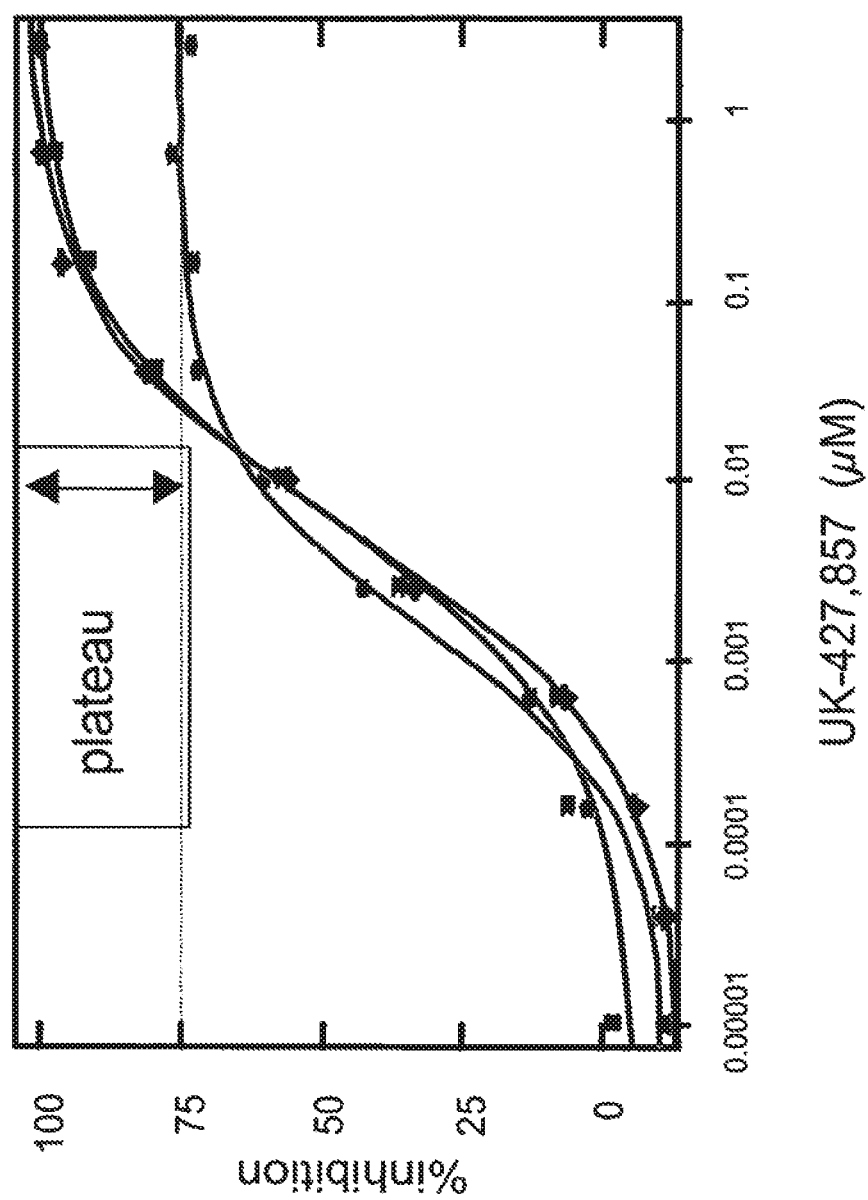

FIG. 8: Noncompetitive entry inhibitor resistance.

FIG. 8 demonstrates log-sigmoid curves for viruses resistant to UK-427,857, indicating that resistance to this entry inhibitor manifests as a reduced maximum percentage of inhibition.

FIG. 9: Reproducibility of inhibition curve plateaus for a noncompetitive Entry inhibitor.

FIG. 9 shows the reproducibility of the maximum percentage of inhibition observed for a representative noncompetitive entry inhibitor, UK-427,857. As show in FIG. 9, multiple measurements of the maximum percentage of inhibition cluster reproducibly.

5. DEFINITIONS

As used herein, the following terms shall have the following meanings:

A "phenotypic assay" is a test that measures a phenotype of a particular virus, such as, for example, HIV, or a population of viruses, such as, for example, the population of HIV infecting a subject. The phenotypes that can be measured include, but are not limited to, the resistance or susceptibility of a virus, or of a population of viruses, to a specific anti-viral agent or that measures the replication capacity of a virus.

A "genotypic assay" is an assay that determines a genotype of an organism, a part of an organism, a population of organisms, a gene, a part of a gene, or a population of genes. Typically, a genotypic assay involves determination of the nucleic acid sequence of the relevant gene or genes. Such assays are frequently performed in HIV to establish, for example, whether certain mutations are associated with drug resistance or resistance or altered replication capacity are present. Genotypes are routinely described as the derived protein sequence encoded by the gene or genes of interest.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-X program, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (O) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Arg (R), Asn (N), Asp (D), Glu (E), Gln (O), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, J. Mol. Biol. 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

A "mutation" is a change in a nucleic acid sequence or in a corresponding amino acid sequence relative to a reference nucleic acid or polypeptide. For embodiments of the invention comprising HIV protease or reverse transcriptase, the reference nucleic acid encoding protease or reverse transcriptase is the protease or reverse transcriptase coding sequence, respectively, present in NL4-3 HIV (GenBank Accession No. AF324493). Likewise, the reference protease or reverse transcriptase polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, Methods in Enzymology 65:499), dideoxy sequencing (Sanger et al., 1977, Proc. Natl. Acad. Sci. USA 74:5463) or hybridization-based approaches (see e.g., Sambrook et al., 2001, Molecular Cloning: A Laboratory Manual, Cold Spring Harbor Laboratory, 3$^{rd}$ ed., NY; and Ausubel et al., 1989, Current Protocols in Molecular Biology, Greene Publishing Associates and Wiley Interscience, NY).

A "mutant" is a virus, gene or protein having a sequence that has one or more changes relative to a reference virus, gene or protein.

The terms "peptide," "polypeptide" and "protein" are used interchangeably throughout.

The term "wild-type" refers to a viral genotype that does not comprise a mutation known to be associated with drug resistance.

The terms "polynucleotide," "oligonucleotide" and "nucleic acid" are used interchangeably throughout.

6. DETAILED DESCRIPTION OF THE INVENTION

In certain aspects, the invention provides a method for determining whether an HIV is resistant to an HIV entry inhibitor. The methods are useful, for example, to guide therapeutic decisions in treatment subjects infected with HIV, whether newly infected or in treatment, including failing treatment, and for screening compounds to identify compounds that will inhibit viruses resistant to other entry inhibitors. Other uses of such methods will be apparent to those of skill in the art.

6.1 Methods for Determining Whether an HIV or HIV Population is Resistant to Entry Inhibitors In one aspect, the invention provides a method for determining whether an HIV is resistant to an HIV entry inhibitor. The methods generally comprise determining phenotypic drug susceptibility of an HIV or an HIV population using, for example, the phenotypic drug susceptibility assays presented in Example 1, and determining whether the HIV or HIV population is resistant to an entry inhibitor as described hereinafter. However, any such susceptibility assay known by one of skill in the art can in principle be used in the methods for determining phenotypic drug susceptibility. Drug susceptibility can be plotted, for example, as percent inhibition versus log$_{10}$ drug concentration and defined based on, for example, the IC$_{50}$ and percent inhibition at the highest drug concentration. Such percent inhibition observed at the highest drug concentration for a reference HIV, such as, for example, HXB2, NL4-3, or SF2, is the maximum percent inhibition (max % inhibition).

In certain embodiments, the methods can be used to identify resistance to entry inhibitors that exhibit competitive kinetics, i.e., compete with viral proteins for access to viral or cellular components that mediate virus entry. Such entry inhibitors include, but are not limited to, T-20 and AMD-3100, discussed above. Viruses that are resistant to such entry inhibitors exhibit an increased IC$_{50}$ relative to susceptible viruses.

In other embodiments, the methods can be used to identify resistance to entry inhibitors that exhibit non-competitive kinetics, i.e., do not directly compete with viral proteins for access to viral or cellular components that mediate entry, but instead alter the conformation of the cellular component and/or viral protein in a manner that disrupts the interaction between such proteins and components. Examples of such non-competitive inhibitors include, but are not limited to, entry inhibitors such as SCH-C, TNX-355, UK-427,857, SCH-D, GW-873,140, and TAK-220. For the first time, Applicants have identified that viruses resistant to such entry inhibitors exhibit non-competitive kinetics for inhibition.

Viruses resistant to such non-competitive entry inhibitors manifest such resistance in at least two different ways. First, viruses resistant to non-competitive entry inhibitors cannot be completely inhibited. That is, there is no concentration of entry inhibitor that can completely inhibit the envelope protein-cell surface receptor interaction. Thus, when a log-sigmoid curve is plotted comparing a measurement of virus entry to drug concentration, the curve plateaus at less than 100% inhibition. As such, where a log-sigmoid curve generated as described herein indicates that no matter how much entry inhibitor is added to the assay mixture, the virus remains able to enter the cell at a detectable level, the virus is resistant to the entry inhibitor.

Second, such viruses exhibit reduced maximum percentages of inhibition relative to susceptible viruses. Thus, by observing that a particular virus or viral population exhibits a reduced maximum percentage of inhibition relative to a reference virus or viral population, it can be determined that the virus or viral population exhibits reduced susceptibility (resistance) to the tested entry inhibitor. The reference virus or viral population can be a virus or viral population obtained from a subject or other source prior to therapy with or exposure to an entry inhibitor. Alternatively, the reference virus or viral population can be a reference strain, such as, for example, SF2, HXB2, or NL4-3. As yet another alternative, the maximum percentage of inhibition observed for the reference virus or viral population can be an average maximum percentage of inhibition derived from a number of viruses or viral populations.

Thus, in certain embodiments, the invention provides a method for determining whether an HIV is resistant to an HIV entry inhibitor that comprises generating a log-sigmoid inhibition curve comprising data points that measure entry of the HIV into a cell in the presence of varying concentrations of the HIV entry inhibitor; and comparing the inhibition curve of step (a) to a log-sigmoid inhibition curve for a reference HIV. In certain embodiments, a decrease in the maximum inhibition percentage observed for the HIV relative to that observed for the reference HIV indicates that the HIV is resistant to the HIV entry inhibitor.

In certain embodiments, the entry inhibitor is selected from the group consisting of BMS-488,403 (Bristol-Meyers Squibb; New York, N.Y.), Pro-542 (Progenics Pharmaceuticals, Inc.; Tarrytown, N.Y.), mAb B4 (United BioMedical, Inc.; Hauppauge, N.Y.), TNX-355 (Tanox Inc.; Houston, Tex.), UK-427,857 (Pfizer Inc.; New York, N.Y.), SCH-D (Schering-Plough; Kenilworth, N.J.), GW-873,140 (GlaxoSmithKline; Research Triangle, NC), AMD-11070 (AnorMED Inc.; Langley, Canada), TAK-220 (Takeda Chemical Industries, Ltd.; Osaka, Japan), Pro-140 (Progenics Pharmaceuticals, Inc.; Tarrytown, N.Y.), and mAb004 (Human Genome Sciences Inc.; Rockville, Md.). In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is selected from the group consisting of SCH-C, SCH-D, UK-427857, and TNX-355. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004. In certain embodiments, the reference HIV is HXB2, NL4-3, or SF2. In certain embodiments, the HIV is from a subject infected with HIV.

In certain embodiments, the data points that measure entry of the HIV into the cell are determined by contacting an HIV viral particle with the cell in the presence of the HIV entry inhibitor, wherein the cell expresses a cell surface receptor to which the viral particle binds, and wherein the viral particle comprises: (i) a viral expression vector that lacks a nucleic acid encoding a viral envelope protein, but which comprises an indicator nucleic acid that produces a detectable signal when introduced into the cell, and (ii) a viral envelope protein encoded by a nucleic acid of the HIV; and measuring the amount of the detectable signal produced by the cell. In certain embodiments, the detectable signal is a fluorescent signal. In certain embodiments, the indicator nucleic acid encodes luciferase. In certain embodiments, the viral particle is produced by co-transfecting into a cell (i) a nucleic acid encoding a viral envelope protein of the HIV, and (ii) a viral expression vector lacking a nucleic acid encoding an envelope protein, wherein the vector comprises an indicator nucleic acid that produces a detectable signal. In certain embodiments, the cell surface receptor is CD4. In certain embodiments, the cell also expresses a chemokine receptor. In certain embodiments, the chemokine receptor is CXCR4 or CCR5. In certain embodiments, the HIV nucleic acid encodes gp160, gp120, or gp41.

In other aspects, the invention provides a method for determining whether an HIV population is resistant to an HIV entry inhibitor that comprises generating a log-sigmoid inhibition curve comprising data points that measure entry of the HIV population into a cell in the presence of varying concentrations of the HIV entry inhibitor; and comparing the inhibition curve of step (a) to a log-sigmoid inhibition curve for a reference HIV population. In certain embodiments, a decrease in the maximum inhibition percentage observed for the HIV population relative to that observed for the reference HIV population indicates that the HIV is resistant to the HIV entry inhibitor.

In certain embodiments, the entry inhibitor is selected from the group consisting of SCH-C, SCH-D, UK-427857, and TNX-355. In certain embodiments, the entry inhibitor is selected from the group consisting of BMS-488,403, Pro-542, mAb B4, TNX-355, UK-427,857, SCH-D, GW-873, 140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004. In certain embodiments, the reference HIV population is an HXB2, NL4-3, or SF2 population. In certain embodiments, the HIV population is from a subject infected with HIV.

In certain embodiments, the data points that measure entry of the HIV population into the cell are determined by contacting a plurality of HIV viral particles with the cell in the presence of the HIV entry inhibitor, wherein the cell expresses a cell surface receptor to which the viral particles bind, and wherein each of the plurality of viral particles comprises: (i) a viral expression vector that lacks a nucleic acid encoding a viral envelope protein, but which comprises an indicator nucleic acid that produces a detectable signal when introduced into the cell, and (ii) a viral envelope protein encoded by a nucleic acid of the HIV population; and measuring the amount of the detectable signal produced by the cell. In certain embodiments, the detectable signal is a fluorescent signal. In certain embodiments, the indicator nucleic acid encodes luciferase. In certain embodiments, each of the plurality of HIV viral particles comprises the same viral envelope protein. In certain embodiments, the plurality of viral particles are produced by co-transfecting into a cell (i) a plurality of nucleic acids each encoding a viral envelope protein of the HIV population, and (ii) a viral expression vector lacking a nucleic acid encoding an envelope protein, wherein the vector comprises an indicator nucleic acid that produces a detectable signal. In certain embodiments, the cell surface receptor is CD4. In certain embodiments, the cell also expresses a chemokine receptor. In certain embodiments, the chemokine receptor is CXCR4 or CCR5. In certain embodiments, the HIV nucleic acid encodes gp160, gp120, or gp41.

In other aspects, the invention provides a method for determining whether an HIV is resistant to an HIV entry inhibitor that comprises determining a log-sigmoid inhibition curve comprising data points for entry of the HIV in the presence of varying concentrations of the HIV entry inhibitor, wherein if the entry of the HIV cannot be completely inhibited by the HIV entry inhibitor, the HIV is resistant to the HIV entry inhibitor.

In certain embodiments, the entry inhibitor is selected from the group consisting of SCH-C, SCH-D, UK-427,857, and TNX-355. In certain embodiments, the entry inhibitor is selected from the group consisting of BMS-488,403, Pro-542, mAb B4, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004. In certain embodiments, the HIV is from a subject infected with HIV.

In certain embodiments, the data points that measure entry of the HIV into the cell are determined by: contacting an HIV viral particle with the cell in the presence of the HIV entry inhibitor, wherein the cell expresses a cell surface receptor to which the viral particle binds, and wherein the viral particle comprises: (i) a viral expression vector that lacks a nucleic acid encoding a viral envelope protein, but which comprises an indicator nucleic acid that produces a detectable signal when introduced into the cell, and (ii) a viral envelope protein encoded by a nucleic acid of the HIV; and measuring the amount of the detectable signal produced by the cell. In certain embodiments, the detectable signal is a fluorescent signal. In certain embodiments, the indicator nucleic acid encodes luciferase. In certain embodiments, the viral particle is produced by co-transfecting into a cell (i) a nucleic acid encoding a viral envelope protein of the HIV, and (ii) a viral expression vector lacking a nucleic acid encoding an envelope protein, wherein the vector comprises an indicator nucleic acid that produces a detectable signal. In certain embodiments, the cell surface receptor is CD4. In certain embodiments, the cell also expresses a chemokine receptor. In certain embodiments, the chemokine receptor is CXCR4 or CCR5. In certain embodiments, the HIV nucleic acid encodes gp160, gp120, or gp41.

In another aspect, the invention provides a method for determining whether an HIV population is resistant to an HIV entry inhibitor, comprising determining a log-sigmoid inhibition curve comprising data points for entry of the HIV population in the presence of varying concentrations of the HIV entry inhibitor, wherein if the entry of the HIV population cannot be completely inhibited by the HIV entry inhibitor, the HIV population is resistant to the HIV entry inhibitor.

In certain embodiments, the entry inhibitor is selected from the group consisting of SCH-C, SCH-D, UK-427,857, and TNX-355. In certain embodiments, the entry inhibitor is selected from the group consisting of BMS-488,403, Pro-542, mAb B4, TNX-355, UK-427,857, SCH-D, GW-873, 140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004. In certain embodiments, the HIV population is from a subject infected with HIV.

In certain embodiments, the data points that measure entry of the HIV population into the cell are determined by contacting a plurality of HIV viral particles with the cell in the presence of the HIV entry inhibitor, wherein the cell expresses a cell surface receptor to which the viral particles bind, and wherein each of the plurality of viral particles comprises: (i) a viral expression vector that lacks a nucleic acid encoding a viral envelope protein, but which comprises an indicator nucleic acid that produces a detectable signal when introduced into the cell, and (ii) a viral envelope protein encoded by a nucleic acid of the HIV population; and measuring the amount of the detectable signal produced by the cell. In certain embodiments, the detectable signal is a fluorescent signal. In certain embodiments, the indicator nucleic acid encodes luciferase. In certain embodiments, each of the plurality of HIV viral particles comprises the same viral envelope protein. In certain embodiments, the plurality of viral particles are produced by co-transfecting into a cell (i) a plurality of nucleic acids each encoding a viral envelope protein of the HIV population, and (ii) a viral expression vector lacking a nucleic acid encoding an envelope protein, wherein the vector comprises an indicator nucleic acid that produces a detectable signal. In certain embodiments, the cell surface receptor is CD4. In certain embodiments, the cell also expresses a chemokine receptor. In certain embodiments, the chemokine receptor is CXCR4 or CCR5. In certain embodiments, the HIV nucleic acid encodes gp160, gp120, or gp41.

In embodiments of the invention where the methods determine whether an HIV population is resistant to an HIV entry inhibitor, the HIV population can be a heterogeneous population. In certain embodiments, the HIV population can be a homogenous population. Preferably, the HIV population corresponds to the population of HIV infecting a subject. For example, by determining the log-sigmoid inhibition curve of many, e.g., 50, 100, or more, individual env isolates from the subject, the resistance or susceptibility of the HIV population infecting the subject can be determined.

In certain embodiments, the indicator nucleic acid comprises an indicator gene. In another embodiment of this invention, the indicator gene is a luciferase gene.

In certain embodiments, the cell surface receptor is CD4. In certain embodiments, the cell surface receptor is a chemokine receptor. In certain embodiments, the cell surface receptor is CXCR4 or CCR5. In certain embodiments, the cell surface receptor is both CXCR4 and CCR5.

In certain embodiments, the subject is infected with the HIV-1 virus, a hepatitis virus (such as the HCV or HBV virus), or any other virus.

In certain embodiments, the nucleic acid comprises DNA encoding gp160, gp120, and/or gp41.

In certain embodiments, the viral expression vector comprises HIV nucleic acid.

In certain embodiments, the viral expression vector comprises an HIV gag-pol gene.

In certain embodiments, the viral expression vector comprises DNA encoding vif, vpr, tat, rev, vpu, and nef.

In certain embodiments, the cell is a mammalian cell. In certain embodiments, the mammalian cell is a human cell. In certain embodiments, the human cell is a human embryonic kidney cell. In certain embodiments, the human embryonic kidney cell is a 293 cell. In certain embodiments, the cell is a human T cell. In certain embodiments, the cell is a human T cell leukemia cell line. In certain embodiments, the cell is a peripheral blood mononuclear cell. In certain embodiments, the cell is an astroglioma cell. In certain embodiments, the astroglioma cell is a U87 cell. In certain embodiments, the cell is a human osteosarcoma cell. In certain embodiments, the human osteosarcoma cell is an HT4 cell. In certain embodiments, the cell is a cell that does not naturally express CD4, CXCR4, and/or CCR5, but has been engineered to express one or more of these receptors. In certain embodiments, the cell has been engineered to express CD4. In certain embodiments, the cell has been engineered to express CXCR4. In certain embodiments, the cell has been engineered to express CCR5.

In certain embodiments, the HIV entry inhibitor binds to the cell surface receptor. In certain embodiments, the compound is a ligand of the cell surface receptor. In certain embodiments, the compound comprises an antibody, or an antigen-binding fragment thereof. In certain embodiments, the compound inhibits membrane fusion. In certain embodiments, the compound is a peptide, a peptidomimetic, an organic molecule, or a synthetic compound. In certain embodiments, the compound binds the viral envelope protein.

In another aspect, the invention provides a method for determining susceptibility of a virus to a compound which inhibits viral cell entry which comprises: (a) obtaining nucleic acid encoding a viral envelope protein from a subject infected by the virus; (b) co-transfecting into a first cell (i) the nucleic acid of step (a), and (ii) a viral expression vector which lacks a nucleic acid encoding an envelope protein, and which comprises an indicator nucleic acid which produces a detectable signal, such that the first cell produces viral particles comprising the envelope protein encoded by the nucleic acid obtained from the subject; (c) contacting the viral particles produced in step (b) with a second cell in the presence of the compound, wherein the second cell expresses a cell surface receptor to which the virus binds; (d) measuring the amount of signal produced by the second cell in order to determine the infectivity of the viral particles; and (e) comparing the amount of signal measured in step (d) with the amount of signal produced in the absence of the compound, wherein a reduced amount of signal measured in the presence of the compound indicates that the virus is susceptible to the compound.

The invention provides a method for determining whether a virus has developed resistance to an entry inhibitor which comprises: (a) determining whether a virus is resistant to an entry inhibitor according a method of the invention, wherein a nucleic acid encoding a viral envelope protein is obtained from a subject at a first time; (b) determining whether a virus is resistant to an entry inhibitor according a method of the invention, wherein the nucleic acid encoding the viral envelope protein is obtained from the subject at a later second time; and (c) comparing the susceptibilities determined in steps (a) and (b), wherein a decrease in susceptibility at the later second time indicates that the virus has developed reduced susceptibility or resistance to the entry inhibitor.

The invention provides for a method for identifying a mutation in a virus that confers resistance to a compound that inhibits viral entry into a cell which comprises: (a) determining the nucleic acid sequence or the amino acid sequence of the virus prior to any treatment of the virus with the compound; (b) obtaining a virus resistant to the compound; (c) determining the nucleic acid sequence or the amino acid sequence of the resistant virus from step (b); and (d) comparing the nucleic acid sequence or the amino acid sequences of steps (a) and (c), respectively, so as to identify the mutation in the virus that confers resistance to the compound.

In certain embodiments, the virus obtained in step (b) is the virus of step (a) grown in the presence of the compound until resistance is developed.

In certain embodiments, the virus obtained in step (b) is isolated from a subject which has been undergoing treatment with the compound.

In certain embodiments, this invention further provides a means and method for discovering, optimizing and characterizing novel or new drugs that target various defined and as yet undefined steps in the virus attachment and entry process.

In certain embodiments, this invention further provides a means and method for discovering, optimizing and characterizing HIV-1 vaccines (either preventative or therapeutic) that target various defined and as yet undefined steps in the virus attachment and entry process.

In certain embodiments, this invention provides a means and method for identifying amino acid substitutions/mutations in HIV-1 envelope proteins (gp41 and/or gp120) that alter susceptibility to inhibitors of virus entry.

In certain embodiments, this invention further provides a means and method for determining HIV-1 envelope amino acid substitutions/mutations that are frequently observed, either alone or in combination, in viruses that exhibit altered susceptibility to virus entry inhibitors.

In certain embodiments, this invention further provides a means and method for using virus entry inhibitor susceptibility to guide the treatment of subjects failing antiretroviral drug treatment.

In certain embodiments, this invention further provides the means and methods for using virus entry inhibitor susceptibility to guide the treatment of subjects newly infected with HIV-1.

In another aspect, the methods comprise determining that a subject is infected with an HIV that is resistant to an HIV entry inhibitor according to a method of the invention, then advising a medical professional of the treatment option of administering to the subject a therapeutic regimen that does not include the HIV entry inhibitor. In certain embodiments, the HIV entry inhibitor is SCH-C, SCH-D, UK-427857, or TNX-355. In certain embodiments, the entry inhibitor is selected from the group consisting of BMS-488,403, Pro-542, mAb B4, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004.

In another aspect, the methods comprise determining that a subject is infected with an HIV that is resistant to an HIV entry inhibitor according to a method of the invention, then advising a medical professional not to treat the subject with the HIV entry inhibitor. In certain embodiments, the HIV entry inhibitor is SCH-C, SCH-D, UK-427857, or TNX-355. In certain embodiments, the entry inhibitor is selected from the group consisting of BMS-488,403, Pro-542, mAb B4, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004.

In still another aspect, the methods comprise determining that a subject is infected with an HIV that is resistant to an HIV entry inhibitor according to a method of the invention, and administering to the subject a combination of anti-HIV agents that does not comprise the HIV entry inhibitor. In certain embodiments, the HIV entry inhibitor is SCH-C, SCH-D, UK-427857, or TNX-355. In certain embodiments, the entry inhibitor is selected from the group consisting of BMS-488,403, Pro-542, mAb B4, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004.

In still another aspect, the methods comprise determining that a subject is infected with an HIV that is hypersusceptible to an HIV entry inhibitor according to a method of the invention, then advising a medical professional of the treatment option of administering to the subject a combination of anti-HIV agents that does not comprise an effective amount of the HIV entry inhibitor. In certain embodiments, the HIV entry inhibitor is SCH-C, SCH-D, UK-427857, or TNX-355. In certain embodiments, the entry inhibitor is selected from the group consisting of BMS-488,403, Pro-542, mAb B4, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is Pro-542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is Pro-140. In certain embodiments, the entry inhibitor is mAb004.

In still another aspect, the methods comprise determining whether a subject is infected with an HIV that is resistant to an HIV entry inhibitor according to a method of the invention at a first time, then determining whether the subject remains infected with an HIV that is resistant to an HIV entry inhibitor according to a method of the invention at a later second time. In other embodiments, the methods comprise determining whether a subject is infected with an HIV that is resistant to an HIV entry inhibitor according to a method of the invention at a first time, then determining whether the subject is infected with an HIV that is no longer resistant to an HIV entry inhibitor according to a method of the invention at a later second time.

6.2 Measuring Resistance to an Entry Inhibitor

In this section, methods for performing single-round infectivity assays assessing the ability of a virus to enter a cell are described. These methods can be used, for example, to determine data points for plotting a log-sigmoid curve to assess whether an HIV is resistant to an entry inhibitor. In one embodiment, an envelope expression vector capable of expressing HIV-1 envelope proteins in transfected cells was constructed. A related expression vectors have been described, including a plasmid (pAmphoEnv) constructed to express amphotropic murine leukemia virus (A-MLV) envelope protein as described in U.S. Pat. No. 5,837,464 and (Petropoulos et al., 2000). The pAmphoEnv vector uses the immediate early gene promoter of human cytomegalovirus (CMV) and the SV40 polyadenlyation signal sequence to produce A-MLV envelope mRNA in transfected cells. The pAmphoEnv plasmid is modified by deleting the A-MLV envelope gene and introducing restriction enzyme cleavage sites that can enable the insertion of viral envelope fragments derived from a variety of isolates, such as HIV-1. In the case of, HIV-1, the envelope open reading frame spans approximately 2,600 nucleotides and encodes the envelope polyprotein, gp160. The gp160 polyprotein is cleaved by a cellular furin-like protease to produce two subunits, gp41 transmembrane protein and gp120 surface protein. HIV-1 envelope expression vectors can be constructed in stages as follows:

6.2.1 Replacing the A-MLV Envelope Nucleic Acid Sequences from the Envelope Expression Vector (pAmphoEnv) with a Multiple Cloning Site Polylinker:

The A-MLV envelope nucleic acid sequences can be deleted from the pAmphoEnv vector by restriction enzyme digestion. The digested vector can be re-circularized by ligation to a duplex oligonucleotide polylinker containing four unique internal restriction sites (a, b, c, d) for insertion of envelope sequences. The ligation reaction can be used to transform *Escherichia coli* and molecular clones containing the correct polylinker sequence can be identified and confirmed by restriction mapping and DNA sequencing, respectively. The introduction of multiple unique cloning sites into the vector can facilitate the insertion of HIV-1 envelope sequences. Restriction sites within the polylinker can be chosen based on their infrequent occurrence in HIV-1 envelope sequences (LANL HIV-1 database). This vector can be referred to as pCX. The functionality of the pCX vector can be demonstrated by inserting a reporter gene or indicator nucleic acid, such as firefly luciferase, into the pCX multiple cloning site and measuring a signal from the indicator nucleic acid or reporter gene activity in transfected cells. As used herein, "indicator nucleic acid" refers to a nucleic acid encoding a protein, DNA or RNA structure that either directly or through a reaction gives rise to a measurable or noticeable signal, e.g. color or light of measurable wavelength, or generation of a specific DNA or RNA structure used as an indicator which could be amplified using any one of a number of quantitative amplification assays.

6.2.2 Inserting Viral Envelope Sequences into the PCX Envelope Expression Vector:

Using mutagenic primers for PCR amplification, viral envelope fragments are generated that contain two unique restriction sites (a, b and c, d, respectively) adjacent to the initiation and termination codons of, for example, the HIV-1 envelope open reading frame. Introduction of two unique restriction sites at each end of the envelope open reading frame can improve chances of cloning HIV-1 envelope fragments harboring internal restriction sites for any one of the enzymes found in the multiple cloning site of the pCX vector.

In the case of HIV-1, two well-characterized molecular clones of HIV-1 with known differences in the envelope gene, NL4-3 (a syncytium-inducing, T-cell tropic, laboratory strain) and JR-CSF (a non-syncytium-inducing, macrophage-tropic, primary isolate) can be used as-template for PCR amplification. The .about.2,600 nucleotide amplification products can be digested with two restriction enzymes (each enzyme cleaving at one end of the fragment; e.g. a and c or b and d) and subsequently inserted into the pCX vector by ligation and transformation of *Escherichia coli*. Molecular clones containing the appropriate envelope sequences can be identified by restriction mapping and confirmed by DNA sequencing. The resulting plasmids, pHIVenv (NL4-3) and pHIVenv (JR-CSF), can be used to express HIV-1 envelope proteins in transfected cells (FIG. 1A). The functionality of the envelope expression vectors, such as the pHIVenv vectors, can be demonstrated by measuring viral envelope synthesis in transfected cells (Western Blot), and by their ability to pseudotype envelope deficient retrovirus vectors. High titer virus stocks using the human embryonic kidney 293 cell line has been demonstrated (Petropoulos et al., 2000), however the present invention is not restricted to those cell lines. Other suitable cell lines used as a first cell for transfection of nucleic acid obtained from the subject encoding a viral envelope protein include, by way an example and not as limitation to the present invention, 5.25; HOX; U87; MT2; PM1; CEM; etc. The cell line optimally will be engineered to express one or more co-receptors.

6.2.3 Modifying the pCX Hector to Improve the Efficiency of Cloning Viral Envelope Sequences:

To improve the cloning efficiency of viral envelope fragments, the pCX expression vector can be modified by inserting a bacterial killer gene cassette (e.g. control of cell death b gene (ccdB) or a member of the hok-killer gene family) under the control of the *Escherichia coli* lac promoter into the multiple cloning site (the et al., 1990; Bernard and Couturier, 1992; Bernard et al., 1993). This modified vector is referred to as pCXccdB. Transcription of the ccdB killer gene is repressed in bacterial strains that express the lac i repressor, such as JM109. This or an equivalent strain can be used to propagate plasmids carrying the ccdB killer gene that are under the control of the lac promoter. Conversely, in this system bacterial strains that do not over express the lac $i^q$ repressor, such as DH5α and Top10, cannot maintain plasmids that express the ccdB gene. Transformants can be killed due to the ccdB activity. DH5a and ToplO cells can be purchased from several vendors (Life Technologies or Invitrogen). Using this selective cloning approach, the parental expression vector is propagated in a lac $i^q$ bacterial strain. The vector is digested with two restriction enzymes that both remove the ccdB gene cassette, and, in the case of HIV-1, are compatible with the insertion of HIV-1 envelope sequences (a, b, c, d). Following ligation of the vector and envelope fragments, a strain of bacteria lacking laciq is transformed. Once transformed, bacteria-containing plasmids in which the viral envelope inserts have replaced the ccdB killer gene can grow. Bacteria containing plasmids that retain or reconstitute the ccdB killer gene can not survive. In this way, the population of transformed bacteria is enriched for plasmids that contain viral envelope inserts, but is lacking in the parental vector containing the ccdB gene. The construction of the pCXccdB vector is not essential to practice the present invention, but it is expected to significantly improve the efficiency of cloning HIV-1 envelope sequences derived from subject samples; thus, the probability of maintaining the heterogeneity of viral sequences can be improved. The structure of the pCXccdB vector can be confirmed by restriction mapping and DNA sequencing.

6.2.4 Inserting Viral Envelope Sequences into the pCXccdB Expression Vector:

The functionality of the pCXccdB vector can be evaluated by setting up ligation reactions containing viral envelope sequences and incompletely digested pCXccdB vector DNA. Following bacterial transformation, plasmid DNA can be prepared from individual bacterial clones and analyzed by restriction digestion for the presence of viral envelope fragments and the absence of ccdB sequences. The feasibility of this approach is tested by amplifying the envelope region from a total of 13 available HIV-1 clones (pCRII-91US005.11, pCRII-91006.10, pCRII-92US657.1, pCRII-92US711.14, pCRII-91US712.4, pCRII-92US714.1, pCRII-91 HT652.11, pCRII-92BR020.4, pCRI-91 HT651.1A, pCRII-92HT593.1, pCRII-92HT594.10, pCRII-92HT596.4, pCRII-92HT599.24), obtainable through the AIDS research reagent reference program (ARRRP), Rockville, Md. Each fragment can be inserted into pCXccdB and the structure of the resulting pHIVenv expression vectors can be confirmed by restriction mapping and/or DNA sequencing. The functionality of each pHIVenv vector can be demonstrated by measuring HIV-1 envelope protein synthesis in transfected cells (Western Blot), and by their ability to pseudotype envelope-deficient retrovirus vectors.

6.3 Construction of a Bio-Safe Viral Expression Vector Comprising Indicator Nucleic Acid in Place of the Encoding the Envelope Protein.

A bio-safe viral vector is constructed to evaluate inhibitors of viral entry according to similar means and methods as described in U.S. Pat. No. 5,837,464 and Petropoulos et al., 2000 used to evaluate inhibitors of PR and RT. The viral expression vector of the present invention can be co-transfected into cells together with the envelope expression vectors (described above) to produce high titer virus stocks. Such virus stocks can be evaluated for susceptibility to inhibitors of virus entry, including antiviral drugs and neutralizing antibodies. In the case of HIV-1, the viral expression vector can be generated from NL4-3, a well-characterized infectious molecular clone of HIV-1. The 5' long terminal repeat (LTR) which controls viral gene expression can be modified so that transcription of the viral genes in transfected cells is driven by the CMV immediate early promoter (Naviaux et al., 1996). Most of the envelope gene can be deleted, but important control elements such as the rev responsive element (RRE) and accessory protein coding regions, (rev, tat) are retained. In place of the deleted envelope sequences, an indicator nucleic acid, such as a firefly luciferase reporter gene cassette that is under the control of CMV promoter-enhancer sequences (FIGS. 1B and 3) is inserted. Virus infection can be monitored by measuring luciferase activity in infected cells. It is conceivable, although unlikely, that inter-plasmid recombination between the retroviral vector and, for example, the pHIVenv sequences in transfected cells may lead to the generation of infectious HIV-1. In effort to generate a biosafe vector, introduction of several genetic alterations in the HIV genome can be made. For example, deletion of most of the envelope gene, while retaining the important control sequence, RRE, and also deletion of the transcriptional enhancer sequences in the U3 region of the 3' LTR of the vector (FIG. 2) can be accomplished. During the replication of the retroviral genome, the U3 region located at the 3' end of the virus genome serves as the template for the U3 region of the 5' LTR of the provirus in infected cells. Such proviruses lack the strong promoter element in the U3 region of the 5' LTR and thus are unable to produce retroviral RNA in infected cells. This self-inactivating (SIN) strategy has been used successfully for several retroviral vector systems, including HIV-1 (Hwang et al., 1997; Miyoshi et al, 1998). In the assay of the present invention, viral gene expression is not required in infected cells because virus infection is measured by a detectable signal produced by the indicator nucleic acid, such as the production of luciferase activity, driven by its own separate promoter (FIG. 1B). Deletion of envelope sequences and the transcriptional enhancer region (U3) can be accomplished by standard molecular cloning procedures, and each deletion can be verified by DNA sequence analysis.

Functionality of this vector, for example in the case of HIV-1, designated pHIVlucΔU3, can be demonstrated by co-transfection of 293 cells with the pHIVenv vector described above. Efficient transcomplementation of viral proteins produced by both vectors in the transfected cells can lead to the production of viral particles. Virus particles can be harvested from the culture supernatants and analyzed by Western-blotting. Virus titers can be quantitated by routine applications of either p24 ELISA, quantitative PCR or TaqMan assays.

It is not necessary to produce a self-inactivating viral expression vector to carry out the present invention, but it is desirable to improve assay reproducibility and biosafety.

6.4 Identification of Suitable Cell Lines which Express Receptors and Co-Receptors and Support Viral Infection.

Different mammalian cell lines that have been described previously and are known to support infection of a particular virus can be evaluated. As discussed herein for one embodiment relating to HIV-1, the assay can be performed by (a) co-transfecting a first cell with pHIVenv and pHIVlucΔU3, (b) harvesting virus after transfection, (c) using this virus to infect a second cell, both in the presence and absence of virus entry inhibitors, and (d) measuring luciferase production in infected cells.

Table 1 lists representative examples of such cell lines evaluated for HIV-1 infection, including the cell line and its associated receptor/co-receptor. Several of these cell lines can be obtained from public cell repositories.

Viral particles harvested from transfected 293 cell cultures can be used to infect a variety of different cell lines. In the case of HIV-1, the pHIVlucΔU3 vector contains deletions in the envelope gene and the U3 promoter-enhancer as described above, therefore infection of a permissive cell line with virus particles produced by this vector is restricted to a single round of replication. This includes (a) virus attachment and entry, mediated by the viral envelope proteins, produced in trans by the pHIVenv vector as described, (b) the conversion of single stranded viral RNA into double stranded DNA by RT, and (c) integration of viral DNA into the host cell genome (provirus formation). The active transcription of viral genes by RNA polymerase II that normally occurs in infected cells following proviral integration can be restricted by deleting essential viral promoter-enhancer sequences in the pHIVlucΔU3 vector. However, this restriction can not interfere with luciferase gene expression in infected cells since this gene is driven independently of viral gene expression using an internal CMV promoter (FIG. 1B). The amount of luciferase activity produced following infection can be used as a measure of viral infectivity.

HIV-1 attachment and entry into host cells requires interaction with a primary receptor (CD4) and one of several co-receptors, most often CCR5 or CXCR4. Cell lines can be screened that are known to express various combinations of CD4, CCR5 and CXCR4. Specifically, cell lines listed in Table 1 that express (a) CD4 plus CCR5, (b) CD4 plus CXCR4, and (c) CD4 plus CCR5 plus CXCR4 are evaluated. Cell lines that express the CD4 receptor alone, or either the CCR5 or CXCR4 co-receptor alone, may serve as useful controls and can be used to evaluate HIV-1 isolates that do not require CD4 binding or that use co-receptors other than CCR5 and CXCR4. The principal criterion for judging cell line suitability can be infectivity as measured by luciferase production ($10^4$-$10^6$ relative light units). In addition, cell lines can be evaluated based on growth rates, viability, stability and other parameters as deemed necessary. Cell lines can be selected that are easy to maintain and for example, produce large amounts of luciferase activity following infection, which can be infected by different envelope receptor tropisms, e.g. CD4/CXCR4 and CD4/CCR5. Additional well-characterized cell lines that support, for example, HIV replication and express the HIV-1 receptor and co-receptors (e.g. CEM-NKr-CCR5; release category a) are available through public repositories such as the ARRRP.

Further, cell lines can be enhanced using standard procedures, such as promoting infection by the addition of polybrene to cells (Porter et al., 1998). For example, in the case of HIV, other potential cell lines can be identified for use with the present invention by infection with HIV-1 laboratory strains and comparing the recombinant virus infectivity titers to those obtained with infectious HIV-1, or by transfecting cells directly with the viral expression plasmids described herein, and scoring for virus production. Accumulation of viral transcripts can be checked by using a quantitative RT-PCR assay. Cell lines suitable for other viruses can be identified in a similar manner.

The present invention can optimize assay conditions and allow for high-throughput testing of subject samples using automation. Sample preparation methods can be optimized to efficiently capture viral genomic and envelope RNAs. RT-PCR conditions can be optimized to enable amplification of patient-derived viral envelope sequences, such as HIV-1 envelope sequences (.about.2,600 base pairs) at low viral loads (.about.500 copies per ml).

6.5 Demonstration of the Utility of the Assay

The utility of the assay of the present invention is demonstrated by the results achieved from: (1) testing for dose-dependent inhibition of viral entry in the presence of well-characterized inhibitors; and the (2) testing for dose-dependent inhibition of infection in the presence of well-characterized HIV-1 neutralizing antibodies.

The following applications for the virus entry assay of the present invention were
  i) detecting inhibition of HIV-1 replication by inhibitors of virus attachment and entry—(including fusion, receptor and co-receptor inhibitors);
  ii) measuring changes in susceptibility to HIV-1 attachment and entry inhibitors;
  iii) detecting neutralization activity of antibodies generated in response to vaccines targeted against HIV-1 envelope proteins; and
  iv) determining co-receptor tropism.

In certain embodiments, the assay can be performed by (a) co-transfecting a first cell with pHIVenv and pHIVlucΔU3 vectors, (b) harvesting virus approximately 48 h after transfection, (c) using this virus to infect a second cell, both in the presence and absence of virus entry inhibitors and (d) measuring luciferase production approximately 48-72 hr. after infection. Dose-dependent inhibition of HIV-1 replication can be evaluated against a wide range of virus entry inhibitor concentrations using a 96-well format. The appropriate concentration range can be determined empirically for each inhibitor. The data can be plotted as the percent inhibition of luciferase activity vs. drug concentration ($\log_{10}$). Data analysis can be performed using computer software. Inhibition curves can be used to determine 50% inhibitory concentrations ($IC_{50}$) for specific drugs or antibodies.

Envelope proteins derived from a variety of well-characterized HIV-1 isolates are evaluated using pHIVenv vectors constructed as described above. To define envelope co-receptor tropism, in the case of HIV-1, infection using cells expressing CD4 plus CXCR4 and CD4 plus CCR5 is evaluated as described above. A wide variety of compounds that are known to inhibit HIV-1 entry (Table 2), including non-specific agents such as sulfonated polyanions (dextran sulfate and heparin) can be used with the assay of the present invention. Chemokines such as Rantes and SDF-1, the natural ligands for the CCR5 and CXCR4 chemokine receptors, respectively (see Alkhatib et al., 1996; Bleul et al., 1996) are also suitable for use with the present invention. Further, virus entry inhibitors such as T-20 and T1249 (Trimeris, Inc.), PRO542 (Progenics), TNX 355 (Tanox) were used to evaluate utility of the assay of the present invention.

Drug toxicity in target cells are evaluated using standard viability or cytotoxicity assays (e.g. dye exclusion, MTS, ATP).

HIV-1 mutants exhibiting reduced susceptibility to the fusion inhibitor T20 (Rimsky et al., 1998) and the genetic determinants (mutations) that enable these viruses to replicate in the presence of drug map within the envelope protein (gp41-TM) have been described. To demonstrate that the assay of the present invention is capable of measuring changes in drug susceptibility (i.e. resistance), (a) pHIVenv vectors are generated that carry these mutant envelope genes, (b) first cells are co-transfected using these vectors and the pHIVlucΔU3 vector, (c) viruses bearing these mutant envelope proteins are harvested, and (d) the viruses are tested for infectivity in the presence of T20. Reduced drug susceptibility to T20 is evaluated by comparing the $IC_{50}$ of viruses bearing mutant enveloped proteins to those that lack the defined drug resistance mutations. Viruses bearing envelope proteins with drug resistance mutations can exhibit higher $IC_{50}$ values than viruses bearing envelope proteins that lack drug resistance mutations, i.e. inhibition can require a higher drug concentration. Drug resistance mutations can be introduced into envelope expression vectors (pHIVenv) using standard site directed mutagenesis techniques according to standard protocols (Petropoulos et al, 2000; Ziermann et al., 2000)

It is widely accepted that effective vaccines that protect against HIV-1 infection should elicit a strong humoral immune response characterized by broadly cross-reactive neutralizing antibodies. Consequently, the serum of vaccinated individuals is routinely evaluated for the presence of high titer neutralizing antibodies targeted against the immunogen. Most recently, using the HIV-1/simian immunodeficiency virus (SIV) chimeric virus macaque model (SHIV), Mascola and colleagues have shown that passive transfer of such neutralizing antibodies led to reduced viral load after mucosal challenge (Mascola et al., 2000). The assay of the present invention can be used to rapidly and reliably determine the viral neutralizing activity of antibodies generated in response to vaccines targeting envelope antigens, such HIV-1 envelope antigens. For example, the assay of the present invention can (a) generate pHIVenv vectors that express a variety of well-characterized envelope proteins, (b) co-transfect a first cell using these vectors and the pHIVlucΔU3 vector, (c) harvest viruses and incubate with serial dilutions of antibody preparations or vaccine serum (d) test these viruses for infectivity in a second cell. Data analysis and $IC_{50}$ determinations can be performed as described previously and in the literature. In the case of HIV-1, viruses can be selected to represent different HIV-1 genetic backgrounds (e.g. clade A, B, C, D, E, F), different cell and co-receptor tropisms (macrophage/CCR5, T-cell/CXCR4), and different envelope properties (syncytium and non-syncytium inducing, laboratory adapted growth or primary isolate) (Table 2). It can be beneficial to prepare stocks of a defined titer from each virus to optimize assay sensitivity and reproducibility by using a virus input of approximately 20-100 $TCID_{50}$/well and making adjustments as necessary. Antibody preparations can be selected based on previously documented neutralization properties, either functional, such as their ability to neutralize primary isolates, or physical, such as their ability to bind specific gp120 or gp41 epitopes (Table 2). The performance of the assay of the present invention can be judged against the activity of these well-characterized antibody reagents in conventional virus neutralization assays as described in the scientific literature. Serum from a broadly representative group of HIV-1 infected individuals can be used to establish an appropriate range of serum dilutions that can maximize assay sensitivity, yet minimize cytotoxicity. Cytoxicity can be evaluated using standard viability or cytotoxicity assays (e.g. dye exclusion, MTS, ATP).

6.6 Computer-Implemented Methods and Compositions for Determining Whether a Virus is Resistant to an Entry Inhibitor In another aspect, the present invention provides computer-implemented methods for determining whether an HIV is resistant to an entry inhibitor. In such embodiments, the methods of the invention are adapted to take advantage of the processing power of modem computers. One of skill in the art can readily adapt the methods in such a manner. Therefore, in certain embodiments, the invention provides a computer-implemented method for determining whether an HIV is resistant to an entry inhibitor comprising inputting phenotypic information into a memory system of a computer, wherein the phenotypic information comprises data points representing the ability of the HIV to enter a cell in the presence of varying concentrations of the HIV entry inhibitor; inputting a correlation between the inability of the HIV entry inhibitor to completely inhibit entry by the HIV and resistance of the HIV to the HIV entry inhibitor, and determining whether the HIV is resistant to the entry inhibitor.

In certain embodiments, the computer-implemented method for determining whether an HIV is resistant to an entry inhibitor comprises inputting phenotypic information into a memory system of a computer, wherein the phenotypic information comprises log-sigmoid inhibition curve comprising data points that measure entry of the HIV into a cell in the presence of varying concentrations of the HIV entry inhibitor; inputting a log-sigmoid inhibition curve for a reference HIV; and comparing the log-sigmoid curve of step (a) to the log-sigmoid curve of the reference HIV, thereby determining whether the HIV is resistant to the entry inhibitor. In certain embodiments, a decrease in the maximum inhibition percentage observed for the HIV relative to that observed for the reference HIV indicates that the HIV is resistant to the HIV entry inhibitor.

In other aspects, the invention provides a computer-implemented method for determining whether an HIV population is resistant to an entry inhibitor that comprises inputting phenotypic information into a memory system of a computer, wherein the phenotypic information comprises data points representing the ability of the HIV population to enter a cell in the presence of varying concentrations of the HIV entry inhibitor; inputting a correlation between the inability of the HIV entry inhibitor to completely inhibit entry by the HIV population and resistance of the HIV population to the HIV entry inhibitor, and determining whether the HIV population is resistant to the entry inhibitor.

In certain embodiments, the computer-implemented method for determining whether an HIV population is resistant to an entry inhibitor comprises inputting phenotypic information into a memory system of a computer, wherein the phenotypic information comprises log-sigmoid inhibition curve comprising data points that measure entry of the HIV population into a cell in the presence of varying concentrations of the HIV entry inhibitor; inputting a log-sigmoid inhibition curve for a reference HIV population; and comparing the log-sigmoid curve of step (a) to the log-sigmoid curve of the reference HIV population, thereby determining whether the HIV population is resistant to the entry inhibitor. In certain embodiments, a decrease in the maximum inhibition percentage observed for the HIV population relative to that observed for the reference HIV population indicates that the HIV population is resistant to the HIV entry inhibitor.

In certain embodiments, the methods further comprise displaying whether the HIV is resistant to an entry inhibitor on a display of the computer. In certain embodiments, the methods further comprise printing whether the HIV is resistant to an entry inhibitor.

In another aspect, the invention provides a tangible medium indicating whether an HIV is resistant to an entry inhibitor produced according to a method of the invention.

In certain embodiments, the tangible medium is a paper document. In certain embodiments, the tangible medium is a computer-readable medium. In certain embodiments, the paper document is a printed document, e.g., a computer print-out. In still another aspect, the invention provides a computer-readable medium comprising data indicating whether an HIV is resistant to an entry inhibitor produced according to a method of the invention.

In yet another aspect, the invention provides a computer-readable medium that comprises data indicating whether an HIV is resistant to an entry inhibitor produced according a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod.™.

In still another aspect, the invention provides an article of manufacture that comprises computer-readable instructions for performing a method of the invention. In certain embodiments, the article of manufacture is a random-access memory. In certain embodiments, the article of manufacture is a fixed disk. In certain embodiments, the article of manufacture is a floppy disk. In certain embodiments, the article of manufacture is a portable memory device, such as, e.g., a USB key or an iPod.™.

In yet another aspect, the invention provides a computer-readable medium that comprises data indicating whether an HIV is resistant to an entry inhibitor and computer-readable instructions for performing a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod.™.

In yet another aspect, the invention provides a computer system that is configured to perform a method of the invention.

7. EXAMPLES

The following examples are presented to further illustrate and explain the present invention and should not be taken as limiting in any regard. Certain of these experiments were also described in U.S. application Ser. Nos. 09/874,475 and 10/077,027, each of which is incorporated by reference in its entirety.

7.1 Example 1

Measuring Phenotypic Drug Susceptibility to Inhibitors of HIV-1 Entry

This example provides a means and method for accurately and reproducibly measuring susceptibility to inhibitors of HIV-1 attachment and entry (heretofore collectively referred to as entry). Based on this example, the means and method for measuring susceptibility to inhibitors of HIV-1 entry can be adapted to other viruses, including, but not limited to other lentiviruses (e.g. HIV-2), other retroviruses (e.g. HTLV-1 and 2), hepadnaviruses (human hepatitis B virus), flaviviruses (human hepatitis C virus) and herpesviruses human cytomegalovirus). This example further provides a means and method for measuring alterations (increases and decreases) in susceptibility to entry inhibitors.

Measurements of entry inhibitor susceptibility are carried out using adaptations of the means and methods for phenotypic drug susceptibility and resistance tests described in U.S. Pat. No. 5,837,464 (International Publication Number WO 97/27319) which is hereby incorporated by reference.

One vector, an example of the envelope expression vector, (pHIVenv) is designed to express the envelope polyprotein (gp160) encoded by subject derived HIV envelope sequences (FIG. 1). Gp160 is subsequently cleaved by a cellular protease to generate the surface (gp120SU) and transmembrane (gp41TM) subunits that comprise the envelope protein on the surface of HIV-1 virus particles. A second vector, an example of the viral expression vector, (either pHIVluc or pHIVlucΔU3) is designed to express genomic and subgenomic viral RNAs and all HIV proteins except the envelope polyprotein (FIGS. 1A-1B).

In this application, patient-derived segment(s) correspond to the coding region (.about.2,600 nucleotides) of the HIV-1 envelope polyprotein (gp160) and represent either (a) envelope sequences amplified by the reverse transcription-polymerase chain reaction method (RT-PCR) using viral RNA isolated from virus derived from HIV-infected individuals, or (b) envelope sequences derived from molecular clones of HIV-1 that contain specific mutations introduced by site directed mutagenesis of a parental molecular clone (typically NL4-3).

Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Superscript II (Invitrogen, Life Technologies) Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into first strand cDNA. The cDNA was then amplified to high copy number using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216-2220) [e.g. Expand High Fidelity PCR System (Taq+Pwo), (Boehringer Mannheim. Indianapolis, Ind.) OR GeneAmp XL PCR kit (Tth+Vent), (Roche Molecular Systems, Inc., Branchburg, N.J.), Advantage-2, (CloneTech).

Oligo-dT was used for reverse transcription of viral RNA into first strand cDNA. Envelope PCR primers, forward primer Xho/Pin and reverse primer Mlu/Xba (Table 3) were used to amplify the patient-derived segments. These primers are designed to amplify the .about.2,600 nucleotide envelope gene encoding the gp160 envelope polyprotein, while introducing Xho I and Pin AI recognition sites at the 5' end of the PCR amplification product, and Mlu I and Xba I sites at the 3' end of the PCR amplification product.

Subject derived segments (2.5 kB envelope sequence amplification product) were inserted into HIV-1 envelope expression vectors using restriction endonuclease digestion, DNA ligation and bacterial transformation methods as described in U.S. Pat. No. 5,837,464 (International Publication Number WO 97/27319), with minor adaptations. The .about.2,600 nucleotide amplification product was digested with either Xho I or Pin AI at the 5' end and either Mlu I or Xba I at the 3' end. The resulting digestion products were ligated, using DNA ligase, into the 5' Xho I/Pin AI and 3' Mlu I/Xba I sites of modified pCXAS or pCXAT expression vectors. The construction of the pCXAS and pCXAT vectors has been described in U.S. Pat. No. 5,837,464 (International Publication Number WO 97/27319)). Modified pCXAS and pCXAT vectors contain a Pin AI restriction site in addition to the Xho I, Mlu I and Xba I restriction sites that exist in pCXAS and pCXAT. The Pin AI site was introduced between the Xho I and Mlu I sites by site directed mutagenesis, such that the four sites are located 5' to 3' in the following order; Xho I, Pin AI, Mlu I and Xba I. In a preferred embodiment, the 2,600 nucleotide amplification products were digested with Pin AI and Mlu I and ligated into the 5' Pin AI site and the 3' Mlu I site of the modified pCXAS expression vector. Ligation reaction products were used to transform *E. coli*. Following a 24-36 h incubation period at 30-37.degree. C., the expression vector plasmid DNA was purified from the *E. coli* cultures. To ensure that expression vector preparations adequately represents the HIV quasi-species present in the serum of a given subject, many (>100) independent *E. coli* transformants were pooled and used for the preparations of pHIVenv plasmid DNA. Vectors that are assembled in this manner for the purposes of expressing subject virus derived envelope proteins are collectively referred to as pHIVenv (FIGS. 1 and 3).

The genomic HIV expression vectors pHIVluc and pHIVlucΔU3 are designed to transcribe HIV genomic RNA and subgenomic mRNAs and to express all HIV proteins except the envelope polyprotein (FIG. 1B). In these vectors, a portion of the envelope gene has been deleted to accommodate a functional indicator gene cassette, in this case, "Firefly Luciferase" that is used to monitor the ability of the virus to replicate in the presence or absence of anti-viral drugs. In pHIVlucΔU3, a portion of the 3' U3 region has been deleted to prevent transcription of viral RNAs from the 5' LTR in infected cells.

Susceptibility assays for HIV-1 entry inhibitors were performed using packaging host cells consisting of the human embryonic kidney cell line 293 (Cell Culture Facility, UC San Francisco, SF, Calif.) and target host cells consisting of a human osteosarcoma (HOS) cell line expressing CD4 (HT4) plus CCR5, and CXCR4, or astrocytoma (U-87) cell lines expressing either CD4 and CCR5 or CD4 and CXCR4.

Drug susceptibility testing was performed using pHIVenv and pHIVluc or pHIVlucΔU3. Pseudotyped HIV particles containing envelope proteins encoded by the subject derived segment were produced by transfecting a packaging host cell (HEK 293) with resistance test vector DNA. Virus particles were collected about 48 h after transfection and were used to infect target cells (HT4/CCR5/CXCR4, or U-87/CD4/CXCR4, or U-87/CD4/CCR5) that express the HIV receptor (i.e. CD4) and co-receptors (i.e. CXCR4, CCR5). After infection (.about.72 h) the target cells are lysed and luciferase activity is measured. HIV must complete one round of replication to successfully infect the target host cell and produce luciferase activity. The amount of luciferase activity detected in the infected cells is used as a direct measure of "infectivity" (FIGS. 1 and 2). If for any reason (e.g. lack of the appropriate receptor or co-receptor, inhibitory drug activity, neutralizing antibody binding), the virus is unable to enter the target cell, luciferase activity is diminished. Drug susceptibility is assessed by comparing the infectivity in the absence of drug to infectivity in the presence of drug. Relative drug susceptibility can be quantified by comparing the susceptibility of the "test" virus to the susceptibility of a well-characterized reference virus (wildtype) derived from a molecular clone of HIV-1, for example NL4-3 or HXB2.

Packaging host cells were seeded in 10-cm-diameter dishes and were transfected one day after plating with pHIVenv and pHIVluc or pHIVlucΔU3. Transfections were performed using a calcium-phosphate co-precipitation procedure. The cell culture media containing the DNA precipitate was replaced with fresh medium, from one to 24 hours, after transfection. Cell culture media containing viral particles was typically harvested 2 days after transfection and was passed through a 0.45-mm filter. Before infection, target cells were plated in cell culture media. Entry inhibitor drugs were typically added to target cells at the time of infection (one day prior to infection on occasion). Typically, 3 days after infection target cells were assayed for luciferase activity using the Steady-Glo reagent (Promega) and a luminometer.

7.2 Example 2

Identifying Envelope Amino Acid Substitutions/Mutations that Alter Susceptibility to Virus Entry Inhibitors This example provides a means and method for identifying mutations in HIV-1 envelope that confer reduced susceptibility/resistance to virus entry inhibitors. This example also provides a means and method for quantifying the degree of reduced susceptibility to entry inhibitors conferred by specific envelope mutations.

Envelope sequences derived from subject samples, or individual clones derived from subject samples, or envelope sequences engineered by site directed mutagenesis to contain specific mutations, are tested in the entry assay to quantify drug susceptibility based on a well-characterized reference standard (e.g. NL4-3, HXB2).

In one embodiment, susceptibility to longitudinal subject samples (viruses collected from the same subject at different timepoints) is evaluated. For example, susceptibility to entry inhibitors is measured prior to initiating therapy, before or after changes in drug treatment, or before or after changes in virologic (RNA copy number), immunologic (CD4$^+$ T-cell counts), or clinical (opportunistic infection) markers of disease progression.

7.2.1 Genotypic Analysis of Subject HIV Samples

Envelope sequences representing subject sample pools, or clones derived from subject pools, can be analyzed by any broadly available DNA sequencing methods. In one embodiment of the invention, subject HIV sample sequences are determined using viral RNA purification, RT/PCR and dideoxynucleotide chain terminator sequencing chemistry and capillary gel electrophoresis (Applied Biosystems, Foster City, Calif.). Envelope sequences of subject virus pools or clones are compared to reference sequences, other subject samples, or to a sample obtained from the same subject prior to initiation of therapy, if available. The genotype is examined for sequences that are different from the reference or pre-treatment sequence and correlated to differences in entry inhibitor susceptibility.

7.2.2 Entry Inhibitor Susceptibility of Site Directed Mutants

Genotypic changes that correlate with changes in fitness are evaluated by constructing envelope expression vectors (pHIVenv) containing the specific mutation on a defined, drug susceptible, genetic background (e.g. NL4-3 reference strain). Mutations may be incorporated alone and/or in combination with other mutations that are thought to modulate the entry inhibitor susceptibility. Envelope mutations are introduced into pHIVenv vectors using any of the broadly available methods for site-directed mutagenesis. In certain embodiments the mega-primer PCR method for site-directed mutagenesis is used (Sarkar, G. and Summer, S. S., 1990). A pHIVenv vector containing a specific envelope mutation or group of mutations are tested using the virus entry assay described in Example 1. Drug susceptibility of the virus containing envelope mutations is compared to the drug susceptibility of a genetically defined drug susceptible virus that lacks the specific mutations under evaluation. Observed changes in entry inhibitor susceptibility are attributed to the specific mutations introduced into the pHIVenv vector.

7.3 Example 3

Measuring Susceptibility to Virus Entry Inhibitors to Guide Treatment Decisions This example provides a means and method for using virus entry inhibitor susceptibility to guide the treatment of HIV-1. This example further provides a means and method for using virus entry inhibitor susceptibility to guide the treatment of subjects that have received previous antiretroviral treatment with a virus entry inhibitor. This invention further provides the means and methods for using virus entry inhibitor susceptibility to guide the treatment of subjects that have not received previous treatment with a virus entry inhibitor.

In one embodiment, the susceptibility of subject's viruses to virus entry inhibitors is used to guide the treatment of subjects failing antiretroviral regimens that include one or more virus entry inhibitors. Treatment failure (also referred to as virologic failure) is generally defined as partially suppressive antiviral treatment resulting in detectable levels of virus, which is typically measured in the subject plasma). Guidance may include, but is not limited to, (a) clarification of available drug treatment options, (b) selection of more active treatment regimens, (c) clarification of the etiology of rising viral load in treated subjects (i.e. poor adherence, drug resistance), and (d) reduction in the use of inactive and potentially toxic drugs. In this embodiment, resistance test vectors are derived from a subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonists (AMD3100, AMD8664, TAK779, PRO542, and peperidinlyl butane compounds) and CD4 antagonists (MAb 5A8). Appropriate treatment decisions are based on the results of the virus entry assay (e.g. see FIG. 4B) and additional relevant laboratory test results and clinical information.

In another embodiment, the susceptibility of subject's viruses to virus entry inhibitors is used to guide the treatment of subjects that have not been previously treated with antiretroviral regimens that include one or more virus entry inhibitors. Guidance may include, but is not limited to, (a) clarification of available drug treatment options, (b) selection of more active treatment regimens, (c) clarification of the baseline susceptibility to virus entry inhibitors, and (d) reduction in the use of inactive and potentially toxic drugs. Determining baseline susceptibility of virus entry inhibitors in treatment naive subjects is important for two reasons. First, the natural susceptibility of viruses to entry inhibitors can vary widely (e.g. see FIG. 4A). Second, the increased use of virus entry inhibitors will undoubtedly result in the generation of drug resistant variants that can be transmitted to newly infected individuals. In this embodiment, resistance test vectors are derived from a subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonist (e.g. AMD3100, AMD8664, TAK-355, PRO542, and peperidin-lyl butane compounds) and CD4 antagonists (MAb 5A8). Appropriate treatment decisions are based on the results of the virus entry assay and additional relevant laboratory test results and clinical information.

7.4 Example 4

Determining Resistance to HIV Entry Inhibitors

This example provides means and methods for determining whether a particular HIV or population of HIV is resistant or susceptible to an entry inhibitor. These means and methods are useful, for example, to guide therapeutic decisions in treatment subjects infected with HIV, whether newly infected or failing treatment, and for screening compounds to identify compounds that will affect viruses resistant to other entry inhibitors. Other uses of such methods will be apparent to those of skill in the art.

The methods generally rely on determining phenotypic drug susceptibility of an HIV or an HIV population using, for example, the phenotypic drug susceptibility assays presented in Example 1. However, any such susceptibility assay known by one of skill in the art can in principle be used in the methods for determining phenotypic drug susceptibility. Drug susceptibility can be plotted, for example, as percent inhibition versus $\log_{10}$ drug concentration and defined based on, for example, the $IC_{50}$ and percent inhibition at the highest drug concentration. Such percent inhibition observed at the highest drug concentration for a reference HIV, such as, for example, SF2, is the maximum percent inhibition (max % inhibition). In this example, the phenotypic drug susceptibility assay of Example 1 was used to determine a log-sigmoid curve showing the resistance of mutant HIV to SCH-C, TNX-355, T-20, and AMD-3100.

Resistance to certain of these entry inhibitors manifests with competitive kinetics, i.e., the inhibitors compete with viral proteins for access to viral or cellular components that mediate virus entry. Such entry inhibitors include, but are not limited to, T-20 and AMD-3100, discussed above. Viruses that are resistant to such entry inhibitors exhibit an increased $IC_{50}$ relative to susceptible viruses. See FIG. 5, demonstrating that T-20- and AMD-3100-resistant HIV exhibit increased $IC_{50}$ for inhibition of entry by these compounds relative to a sensitive reference virus, and FIG. 7, that such increased $IC_{50}$ relative to sensitive viruses can be observed in mixed populations of viruses.

Resistance to certain of these entry inhibitors manifests with non-competitive kinetics, i.e., the inhibitors do not directly compete with viral proteins for access to viral or cellular components that mediate entry, but instead alter the conformation of the cellular component and/or viral protein in a manner that disrupts the interaction between such proteins and components. Such entry inhibitors include, but are not limited to, UK-427857, SCH-C, SCH-D, UK-427857, and TNX-355. Viruses that are resistant to such non-competitive entry inhibitors exhibit reduced maximum percentages of inhibition relative to susceptible viruses. See FIG. 6, demonstrating that viruses resistant to SCH-C and TNX-355 exhibit reduced maximum percentages of inhibition relative to sensitive viruses, FIG. 8, demonstrating that viruses resistant to UK-427,857 exhibit reduced maximum percentages of inhibition relative to sensitive viruses, and FIG. 7, demonstrating that such reduced maximum percentages of inhibition relative to sensitive viruses can be observed in mixed populations of viruses. Such viruses resistant to non-competitive entry inhibitors can also be detected because such viruses cannot be completely inhibited with high concentrations of the inhibitor. That is, no matter how much inhibitor is added to the assay mixture, entry of viral particles expressing the resistant envelope proteins could be detected.

Finally, the reductions in maximum percentage of inhibition observed for resistant virus were reproducible. FIG. 9 shows the maximum percentage of inhibition determined as described above for particular viral isolates repeated 9 times. As shown in FIG. 9, the maximum percentage of inhibition observed for a particular isolate clustered well, indicating that the assays for determining the maximum percentage inhibition are reproducible.

8. REFERENCES

Adachi, A., H. E. Gendelman, S. Koenig, T. Folks, R. Caney, A. Rabson, and M. A. Martin. 1986. Production of Acquired Immunodeficiency Syndrome-associated Retrovirus in Human and Nonhuman Cells Transfected with an Infectious Molecular Clone. J. Virol. 59:284-291.

Alkhatib, G., C. Combadiere, C. C. Broder, Y. Feng, P. E. Kennedy, P. M. Murphy, and E. A. Berger. 1996. CC CKR5: A Rantes, MIP-1alpha, MIP-1 Beta Receptor as a Fusion Cofactor for Macrophage-tropic HIV-1. Science 272:1955-8.

Allaway G. P., Ryder A. M., Beaudry G. A., and Maddon P. J. 1993. Synergistic Inhibition of HIV-1 Envelope-Mediated Cell Fusion by CD4-based Molecules in Combination with Antibodies to Gp120 or Gp41. Aids Res. Hum. Retroviruses 9:581-7.

Baba, M., O. Nishimura, N. Kanzaki, M. Okamoto, H. Sawada, Y. Iizawa, M. Shiraishi, Y. Aramaki, K. Okonogi, Y. Ogawa, K. Meguro, and M. Fujino. 1999. A Small-molecule, Nonpeptide CCR5 Antagonist with Highly Potent and Selective Anti-hiv-1 Activity. Proc. Natl. Acad. Sci. USA 96:5698-703.

Baxter, J., D. Mayers, D. Wentworth, J. Neaton, and T. Merigan. 1999. A Pilot Study of the Short-term Effects of Antiretroviral Management Based on Plasma Genotypic Antiretroviral Resistance Testing (Gart) in Subjects Failing Antiretroviral Therapy. Presented at the 6th Conference on Retroviruses and Opportunistic Infections. Chicago, Ill.

Bernard P., Kezdy K. e., Van Melderen L., Steyaert J., Wyns L., Pato M. L., Higgins P. N., and Couturier M. 1993. The F Plasmid CcdB protein Induces Efficient ATP-dependent Dna Cleavage by Gyrase. J. Mol. Biol. 23:534-41.

Bernard, P. and Couturier, M. 1992. Cell Killing by the F Plasmid Ccdb protein Involves Poisoning of DNAtopoisomerase II Complexes. J. Mol. Bio. 226:735-45.

Bleul, C. C., M. Farzan, H. Choe, C. Parolin, I. Clark-Lewis, J. Sodroski, and T. A. Springer. 1996. The Lymphocyte Chemoattractant Sdf-1 Is a Ligand for Lestr/fusin and Blocks Hiv-1 Entry. Nature 382:829-33.

Bridger G. J, Skerlj R. T., Padmanabhan S., Martellucci S. A., Henson G. W., Struyf S., Witvrouw M., Schols D., and De Clercq E. 1999. Synthesis and Structure-activity Relationships of Phenylenebis(methylene)-linked Bis-azamacrocycles That Inhibit HIV-1 and HIV-2 Replication by Antagonism of the Chemokine Receptor CXCR4. J. Med. Chem. 42:3971-81.

Carpenter, C. J., Cooper D. A., Fischl, M. A., Gatell J. M., Gazzard B. G., Hammer S. M., Hirsch M. S., Jacobsen D. M., Katzenstein D. A., Montaner J. S., Richman D., Saag M. S., Schechter M., Schooley R. T., Thompson M. A., Vello S., Yeni P. G., and Volberding P. A. 2000. Antiretroviral Therapy in Adults. JAMA 283:381-89.

CDC (Centers for Disease Control and Prevention). HIV/AIDS Surveillance Report, 1999; 11(no. 1).

Coffin, J. M. 1995. HIV Population Dynamics in Vivo: Implications for Genetic Variation, Pathogenesis, and Therapy. Science 267:483-489.

DHHS (Department of Health and Human Services). Henry Kaiser Family Foundation: Guidelines for the Use of Antiretrovirals Agents in HIV-infected Adults and Adolescents. (Jan. 28, 2000).

Gerdes, K., L. K. Poulsen. T. Thisted, A. K. Nielson, J. Martinussen, and P. H. Andreasen. 1990. The Hok Killer Gene Family in Gram-negative Bacteria. The New Biologist: 2:946-956.

Hertogs, K., M. P. De Bethune, V. Miller, T. Ivens, P. Schel, A. V. Cauwenberge, C. Van Den Eynde, V. Van Gerwen, H. Azijn, M. Van Houtte, F. Peeters, S. Staszewski, M. Conant, S. Bloor, S. Kemp, B. Larder, and R. Pauwels. 1998. A Rapid Method for Simultaneous Detection of Phenotypic Resistance to Inhibitors of protease and Reverse Transcriptase in Recombinant Human Immunodeficiency Virus Type 1 Isolates from Subjects Treated with Antiretroviral Drugs. Antimicrob. Agents Chemother. 42:269-276.

Hwang, J.-j., L. Li, W. f. Anderson. 1997. A Conditional Self-inactivating Retrovirus Vector That Uses a Tetracycline-responsive Expression System. J. Virol. 71: 7128-7131.

Japour, A. J., D. L. Mayers, V. A. Johnson, D. R. Kuritzkes, L. A. Beckett, J. M. Arduino, J. Lane, B. R. J., P. S. Reichelderfer, R. T. D-aquila, C. S. Crumpacker, T. R.-S. Group, T.A.C.T. Group, and V.C.R.W. Group. 1993. Standardized Peripheral Blood Mononuclear Cell Culture Assay for Determination of Drug Susceptibilities of Clinical Human Immunodefiency Virus Type 1 Isolates. Antimicrob. Agents Chemother. 37:1095-1101.

Judice J. K., Tom J. Y., Huang W., Wrin T., Vennari J., Petropoulos C. J., and Mcdowell R. S. 1997. Inhibition HIV Type 1 Infectivity by Constrained Alphahelical Peptides: Implications for the Viral Fusion Mechanism. Proc. Natl. Acad. Sci. USA 94:13426-30.

Kilby J M, Hopkins S, Venetta Tm, Dimassimo B, Cloud Ga, Lee Jy, Alldrdge L, Hunter E, Lambert D, Bolognesi D, Matthews T, Johnson Mr. Nowak Ma, Shaw Gm, and Saag Ms. 1998. Potent Suppression of HIV-1 Replication in Humans by T-20, a Peptide Inhibitor of Gp41-mediated Virus Entry. Nat Med. 4:1302-7.

Mascola, J. R., G. Stiegler, T. C. Vancott, H. Katinger, C. B. Carpenter, C. E. Hanson, H. Beary, D. Hayes, S. S. Frankel, D. L. Birx, and M. G. Lewis. 2000. Protection of Macaques Against Vaginal Transmission of a Pathogenic HIV-1/siv Chimeric Virus by Passive Infusion of Neutralizing Antibodies. Nature Med. 6:207-210.

Miyoshi, H., B. Ulrike, M. Takahashi, F. H. Gage, and I. M. Verma. 1998. Development of a Self-inactivating Lentivirus Vector. J. Virol. 72:8150-5157.

Naviaux, R. K., E. Costanzi, M. Haas, and I. M. Verma. 1996. The Pcl Vector System: Rapid production of Helper-free, High-titer, Recombinant Retroviruses. J. Virol. 70: 5701-5705.

Petropoulos, C. J., N. T. Parkin, K. L. Limoli, Y. S. Lie, T. Wrin, W. Huang, H. Tian, D. Smith, G. A. Winslow, D. Capon and J. M. Whitcomb. 2000. A Novel Phenotypic Drug Susceptibility Assay for HIV-1. Antimicrob. Agents & Chem. 44:920-928.

Phrrma (Pharmaceutical Research and Manufacturers of America). New Medicines in Development for Aids 1999.

Piketty, C., E. Race, P. Castiel, L. Belec, G. Peytavin, A. si-mohamed, G. Gonzalez-canali, L. Weiss, F. Clavel, and M. Kazatchkine. 1999. Efficacy of a Five-drug Combination Including Ritonavir, Saquinavir and Efavirenz in Subjects Who Failed on a Conventional Triple-drug Regimen: Phenotypic Resistance to protease Inhibitors predicts Outcome of Therapy. Aids: 13:f71-f77.

Porter, C. C., K. V. Lukacs, G. Box, Y. Takeuchi, and M. K. L. Collins. 1998. Cationic Liposomes Enhance the Rate of Transduction by a Recombinant Retroviral Vector in Vitro and in Vivo. J. Virol. 72:4832-4840.

Reimann K. A., Cate R. L., Wu Y., Palmer L., Olson D., Waite B. C., Letvin N. L., and Burkly L. C. 1995. In Vivo Administration of CD4-specific Monoclonal Antibody: Effect on provirus Load in Rhesus Monkeys Chronically Infected with the Simian Immunodeficiency Virus of Macaques. Aids Res. Hum. Retroviruses 11:517-25.

Retroviruses. Coffin, J., S. Hughes, H. Varmus (Eds). 1997. Cold Spring Harbor Laboratory Press, Cold Spring Harbor, N.Y.

Richman, D. 1998. Nailing down Another HIV Target. Nature Med. 4:1232-1233.

Rimsky, L. T., D. C. Shugars, and T. J. Matthews. 1998. Determinants of Human Immunodeficiency Virus Type 1 Resistance to Gp41-derived Inhibitory Peptides. J. Virol. 72:986-993.

Rodriguez-Rosado, R., Briones, C. and Soriano, V. 1999. Introduction of HIV Drug-resistance Testing in Clinical Practice. Aids 13:1007-1014.

Schinazi, R. F., Larder, B. A., and Mellors, J. W. 1999. Mutations in Retroviral Genes Associated with Drug Resistance. Intl. Antiviral News: 7:46-49.

Shi C., and J. W. Mellors. 1997. A Recombinant Retroviral System for Rapid in Vivo Analysis of Human Immunodefiency Virus Type 1 Susceptibility to Reverse Transcriptase Inhibitors. Antimicrob. Agents Chemother 41:2781-2785.

Schurmann D et al. SCH D: antiviral activity of a CCR5 receptor antagonist. Eleventh Conference on Retroviruses and Opportunistic Infections, San Francisco, abstract 140LB, 2004.

Stephenson, J. 1999. New Class of Anti-HIV Drugs. Jama 282:1994.

Who, Unaids/World Health Organization. Report: Aids Epidemic Update: December 1999.

Wild, C., T. Oak, C. Mcdanal, D. Bolognesi, and T. Matthews. 1992. A Synthetic Peptide Inhibitor of HIV Replication: Correlation Between Solution Structure and Viral Inhibition. Proc. Natl. Acad. Sci. USA 89:10537-10541.

Zennou, V., F. Mammamo, S. Paulous, D. Mathez, and F. Calvel. 1998. Loss of Viral Fitness Associated with Multiple Gag and Gag-pol processing Defects in Human Immunodefiency Virus Type 1 Variants Selected for Resistance to Protease Inhibitors in vivo. J. Virol. 72:3300-06.

Ziermann, R., K. Limoli, K. Das, E. Arnold, C. J. Petropoulos, and N. T. Parkin. 2000. A Mutation in HIV-1 Protease, N88s, That Causes in Vitro Hypersensitivity to Amprenavir. J. Virol. 74:4414-4419.

TABLE 1

Cells

| Cell | Receptor |
|---|---|
| 5.25 | CXCR4, CD4, CCR5 (not expressed well) BONZO |
| 5.25.Luc4.M7 | CD4, CCR5, BONZO |
| HOS.CD4.CCR5 | CD4, CCR5 |
| HOS.CD4.CXCR4 | CD4, CXCR4 |
| HOS.CD4 | CD4, low level expression of CCR5 and CXCR4 |
| HOS HT4 R5 GFP wt | CD4, CXCR4, CCR5 |
| HOS.CD4.CCR5.GFP.M7#6* | CD4, CXCR4, CCR5 |
| P4.CCR5 | CD4, CXCR4, CCR5 |
| U87.CD4 | CD4 |
| U87.CD4 R5 | CD4, CCR5 |
| U87.CD4 X4 | CD4, CXCR4 |
| MT2 | CD4, CXCR4 |
| MT4 | CD4, CXCR4 |
| PM1 | CD4, CXCR4, CCR5 |
| CEM NKr CCR5 | CD4, CXCR4, CCR5 |

TABLE 2

Representative viruses and reagents

| Viruses | Envelope[a] | Source |
|---|---|---|
| 89.6, SF2 | R5-X4/SI/B | ARRRP[B] |
| 92BR014, 92US076 | R5-X4/SI/B | ARRRP |
| JR-CSF, 91US005 | R5/NSI/B | ARRRP |
| 91US054 | SI/B | ARRRP |
| NL43, MN, ELI | X4/B | ARRRP |
| 92HT599 | X4 | ARRRP |
| 92UG031 | R5/NSI/A | ARRRP (IN-HOUSE) |
| 92TH014, 92TH026 | R5/NSI/B | ARRRP (IN-HOUSE) |
| 92BR025, 93MW959 | R5/SI/C | ARRRP (IN-HOUSE) |
| 92UG035 | R5/NSI/D | ARRRP (IN-HOUSE) |
| 92TH022, 92TH023 | R5/NSI/E | ARRRP (IN-HOUSE) |
| 93BR020 | R5-X4/SI/F | ARRRP (IN-HOUSE) |
| Antibodies | Epitope | SOURCE |
| Mabs 2F5, 1577 | gp41 TM | ARRRP |
| Mabs IG1b12, 2G12, 17b, 48D | gp120 SU | ARRRP |
| Neutralization sera #2, HIV-IG | Polyclonal | ARRRP |
| Entry inhibitors | Target | Source |
| CD4-IG | gp120 SU | Genentech |
| CD4-IGG2 | gp120 SU | Adarc |
| SCD4 | Sigma | Progenics |
| T20 (DP178) | gp41 TM | Trimeris |
| Rantes, MIP1a/b | CCR5 | SIGMA/ARRRP |
| SDF1a/b | CXCR4 | SIGMA/ARRRP |
| AMD 3100 | CXCR4 | AnorMed |
| Dextran sulfate, Heparin | Non-specific | Sigma |

[a]R5 (CCR5 co-receptor), X4 (CXCR4 co-receptor) SI (syncytium inducing), NSI (non-syncytium inducing), A, B, C, D, E, F (envelope clade designation)
[B]AIDS Research and Reference Reagent Program

TABLE 3

Primers Tested for the Amplification of HIV Envelope

RT PRIMERS

| | |
|---|---|
| Primer 1 | 5'-GGA GCA TTT ACA AGC AGC AAC ACA GC-3' |
| Primer 2 | 5'-TTC CAG TCA VAC CTC AGG TAC-3' |
| Primer 3 | 5'-AGA CCA ATG ACT TAY AAG G-3' |

5' PCR PRIMERS

| | |
|---|---|
| Primer 4 | 5'-GGG CTC GAG ACC GGT CAG TGG CAA TGA GAG TGA AG-3' |
| Primer 5 | 5'-GGG CTC GAG ACC GGT GAG CAG AAG ACA GTG GCA ATG A-3' |
| Primer 6 | 5'-GGG CTC GAG ACC GGT GAG CAG AAG ACA GTG GCA ATG-3' |

3' PCR PRIMERS

| | |
|---|---|
| Primer 7 | 5'-GGG TCT AGA ACG CGT TGC CAC CCA TCT TAT AGC AA-3' |
| Primer 8 | 5'-GGG TCT AGA ACG CGT CCA CTT GCC ACC CAT BTT ATA GC-3' |
| Primer 9 | 5'-GGG TCT AGA ACG CGT CCA CTT GCC ACC CAT BTT A-3' |
| Primer 10 | 5'-GAT GGT CTA AGA CGC TGT TCA ATA TCC CTG CCT AAC TC-3' |

---

The invention claimed is:

1. A method for treating a patient having an infection with a population of human immunodeficiency virus (HIV) viral particles, comprising:
   (a) contacting or having contacted a plurality of HIV viral particles from a patient having an infection with a first population of HIV viral particles with a cell in the presence of an HIV entry inhibitor, wherein the plurality of HIV viral particles were obtained from the patient at a first time point, wherein the cell expresses a cell surface receptor to which the viral particles bind, and wherein the cell or the viral particle comprises an indicator nucleic acid that produces a detectable signal when the viral particle enters into the cell,
   (b) collecting or having collected data points that measure entry of the first HIV population into the cell by measuring the amount of the detectable signal produced by the cell in the presence of varying concentrations of the HIV entry inhibitor;
   (c) generating a log-sigmoid inhibition curve comprising the data points showing the maximum inhibition percentage for the first HIV population;
   (d) comparing the maximum inhibition percentage of the inhibition curve of step (c) to the maximum inhibition percentage of a log-sigmoid inhibition curve for a second HIV population, wherein the second HIV population comprises a plurality of HIV viral particles that were later obtained from the patient at a second time point;
   (e) determining that the second HIV population has reduced susceptibility to the HIV entry inhibitor if the maximum inhibition percentage observed for the second HIV population is lower than the maximum inhibition percentage observed for the first HIV population or if the entry of the second HIV population cannot be completely inhibited by the HIV entry inhibitor; and
   (f) treating the patient with an effective amount of the HIV entry inhibitor if the maximum inhibition percentage observed for the second HIV population is the same as or higher than the maximum inhibition percentage observed for the first HIV population or if the entry of the second HIV population can be completely inhibited by the HIV entry inhibitor, or treating the patient with an effective amount of a different HIV entry inhibitor or other HIV inhibitor if the maximum inhibition percentage observed for the second HIV population is lower than the maximum inhibition percentage observed for the first HIV population or if the entry of the second HIV population cannot be completely inhibited by the HIV entry inhibitor.

2. The method of claim 1, wherein the patient has been treated with an HIV inhibitor between the first and second time points.

3. The method of claim 2, wherein the HIV inhibitor is an entry inhibitor.

4. The method of claim 1, wherein each of the plurality of viral particles comprises: (i) a viral expression vector that lacks a nucleic acid encoding a viral envelope protein, but which comprises an indicator nucleic acid that produces a detectable signal when introduced into the cell, and (ii) a viral envelope protein encoded by a nucleic acid of the first or second HIV population.

5. The method of claim 1, wherein the indicator nucleic acid encodes luciferase.

6. The method of claim 1, wherein the plurality of viral particles are produced by co-transfecting into a cell: (i) a plurality of nucleic acids, each encoding a viral envelope protein of the first or second HIV population, and (ii) a viral expression vector lacking a nucleic acid encoding an envelope protein, wherein the vector comprises an indicator nucleic acid that produces a detectable signal.

7. The method of claim 1, wherein the cell surface receptor is CD4.

8. The method of claim 1, wherein the cell surface receptor is CD4, and the cell further comprises a coreceptor, wherein the coreceptor is at least one of CXCR4 or CCR5.

9. The method of claim 1, wherein the HIV viral particle comprises a gp160, gp120, gp41, or fragment thereof from an HIV from the patient.

10. The method of claim 1, wherein the cell comprises the indicator nucleic acid that produces a detectable signal when the viral particles enter into the cell.

11. The method of claim 1, wherein the entry inhibitor is an antibody, fragment thereof, or combination of antibody fragments.

12. The method of claim 11, wherein the antibody binds to the HIV envelope surface glycoprotein (gp120).

13. The method of claim 11, wherein the antibody binds to the CD4 binding site, the variable region 3 (V3), the variable region 2 (V2), or a conformational epitope of the HIV envelope surface glycoprotein.

14. The method of claim 11, wherein the antibody binds to the HIV envelope transmembrane glycoprotein (gp41).

15. The method of claim 14, wherein the antibody binds to the membrane proximal external region (MPER) of the HIV envelope transmembrane glycoprotein.

\* \* \* \* \*